United States Patent [19]
Cohen et al.

[11] Patent Number: 6,140,128
[45] Date of Patent: Oct. 31, 2000

[54] PREPARATION OF CALCIUM PHOSPHATE TRANSFECTACONS

[75] Inventors: Darien L. Cohen, Oakland; David W. Kahn, Foster City; Marjorie E. Winkler, Burlingame, all of Calif.

[73] Assignee: Genentech, Inc., South San Francisco, Calif.

[21] Appl. No.: 09/467,723

[22] Filed: Dec. 20, 1999

Related U.S. Application Data
[60] Provisional application No. 60/113,614, Dec. 23, 1998.

[51] Int. Cl.[7] ...................................................... C12N 15/64
[52] U.S. Cl. ........................ 435/455; 435/320.1; 536/23.1
[58] Field of Search ................................ 435/320.1, 455; 536/23.1

[56] References Cited

U.S. PATENT DOCUMENTS

| | | |
|---|---|---|
| 5,484,720 | 1/1996 | Wurm et al. . |
| 5,593,875 | 1/1997 | Wurm et al. . |
| 5,633,156 | 5/1997 | Wurm et al. . |
| 5,686,263 | 11/1997 | Wurm . |
| 5,981,735 | 11/1999 | Thatcher et al. . |

FOREIGN PATENT DOCUMENTS 61-257931  11/1986  Japan .

OTHER PUBLICATIONS

Bacchetti and Graham, "Transfer of the gene for thymidine kinase to thymidine kinase–deficient human cells by purified herpes simplex viral DNA" *Proc. Natl. Acad. Sci. USA* 74(4):1590–1594 (Apr. 1977).

Chen et al., "High–efficiency transformation of mammalian cells by plasmid DNA" *Molecular & Cellular Biology* 7(8):2745–2752 (1987).

Coonrod et al., "On the mechanism of DNA transfection: efficient gene transfer without viruses" *Gene Therapy* 4(12):1313–1321 (Dec. 1997).

Gaunitz et al., "Transient transfection of primary cultured hepatocytes using $CaPO_4$/DNA precipitation" *Biotechniques* 20(5):826–832 (May 1996).

Graham et al., "A New Technique for the Assay of Infectivity of Human Adenovirus 5 DNA" *Virology* 52:456–467 (1973).

Graham et al., "Size and location of the transforming region in human adenovirus type 5 DNA" *Nature* 251(5477):687–691 (Oct. 25, 1974).

Hofland et al., "Formation of stable cationic lipid/DNA complexes for gene transfer" *Proc. Natl. Acad. Sci. USA* 93(14):7305–7309 (Jul. 9, 1996).

Itani et al., "A simple and efficient liposome method for transfection of DNA into mammalian cells grown in suspension" *Gene* 56(2–3):267–276 (1987).

Jordan et al., "Calcium–phosphate mediated DNA transfer into HEK–293 cells in suspension: control of physicochemical parameters allows transfection in stirred media" *Cytotechnology* 26:39–47 (1998).

Jordan et al., "Transfecting mammalian cells: optimization of critical parameters affecting calcium–phosphate precipitate formation" *Nucleic Acids Research* 24(4):596–601 (Feb. 15, 1996).

Loyter et al., "Mechanisms of DNA entry into mammalian cells. II. Phagocytosis of calcium phosphate DNA co–precipitate visualized by electron microscopy" *Experimental Cell Research* 139(1):223–234 (May 1982).

Loyter et al., "Mechanisms of DNA uptake by mammalian cells: fate of exogenously added DNA monitored by the use of fluorescent dyes" *Proc. Natl. Acad. Sci. USA* 79(2):422–426 (Jan. 1982).

McCutchan and Pagano, "Enhancement of the infectivity of simian virus 40 deoxyribonucleic acid with diethylamino-ethyl–dextran" *Journal of the National Cancer Institute* 41(2):351–357 (Aug. 1968).

O'Mahoney and Adams, "Optimization of Experimental Variables Influencing Reporter Gene Expression in Hepatoma Cells Following Calcium Phosphate Transfection" *DNA and Cell Biology* 13(12):1227–1232 (1994).

Orrantia and Chang, "Intracellular distribution of DNA internalized through calcium phosphate precipitation" *Experimental Cell Research* 190(2):170–174 (Oct. 1990).

Orrantia et al., "Energy dependence of DNA–mediated gene transfer and expression" *Somatic Cell & Molecular Genetics* 16(4):305–310 (Jul. 1990).

Parasrampuria, D., "Therapeutic Delivery Issues in Gene Therapy, Part 1: Vectors" *BioPharm* 3:38–45 (Mar. 1998).

Parker and Stark, "Regulation of simian virus 40 transcription: sensitive analysis of the RNA species present early in infections by virus or viral DNA" *Journal of Virology* 31(2):360–369 (Aug. 1979).

Sambrook et al. *Molecular Cloning: A Laboratory Manual*, 2nd edition, Cold Spring Harbor, New York:Cold Spring Harbor Laboratory Press pp. 16.32–16.40 (1989).

Seelos, C., "A critical parameter determining the aging of DNA–calcium–phosphate precipitates" *Analytical Biochemistry* 245(1):109–111 (Feb. 1997).

(List continued on next page.)

*Primary Examiner*—James Ketter
*Attorney, Agent, or Firm*—Janet E. Hasak

[57] ABSTRACT

A process is described for preparing transfectacons, or particles, of calcium phosphate and a desired nucleic acid comprising admixing calcium divalent cation, phosphate multivalent anion, and the desired nucleic acid to form a precipitation mixture, wherein the precipitation mixture comprises an initial phosphate anion concentration of about 0.2 to 0.5 mM; and incubating the precipitation mixture for about 10 to 60 minutes to form transfectacons comprising calcium phosphate and the desired nucleic acid. A process is also provided for delivering desired nucleic acid to eukaryotic tissue or cells comprising introducing to the tissue or cells the transfectacons so prepared. Additionally, a process is disclosed for introducing a desired nucleic acid into a eukaryotic host cell comprising the above two steps, followed by diluting the precipitation mixture and admixing it with a eukaryotic host cell lacking a cell wall to form a transfection mixture; and incubating the transfection mixture to allow the eukaryotic host cell to take up the transfectacons to form a transfected cell.

24 Claims, 4 Drawing Sheets

OTHER PUBLICATIONS

Song and Lahiri, "Efficient transfection of DNA by mixing cells in suspension with calcium phosphate" *Nucleic Acids Research* 23(17):3609–3611 (Sep. 11, 1995).

Strain and Wyllie, "The uptake and stability of simian–virus–40 DNA after calcium phosphate transfection of CV–1 cells" *Biochemical Journal* 218(2):475–482 (Mar. 1, 1984).

Templeton et al., "Improved DNA: liposome complexes for increased systemic delivery and gene expression" *Nature Biotechnology* 15(7):647–652 (Jul. 1997).

Wigler et al., "Biochemical transfer of single–copy eucaryotic genes using total cellular DNA as donor" *Cell* 14:725–731 (1978).

Wilson et al., "Optimization of calcium phosphate transfection for bovine chromaffin cells: relationship to calcium phosphate precipitate formation" *Analytical Biochemistry* 226(2):212–220 (Apr. 10, 1995).

Yang and Yang, "Characterization of calcium phosphate as a gene carrier (I): electrochemical properties" *Drug Delivery* 3:173–179 (1996).

Yang and Yang, "Characterization of calcium phosphate as a gene carrier (II): zeta potential and DNA transfection" *Drug Delivery* 3:181–186 (1996).

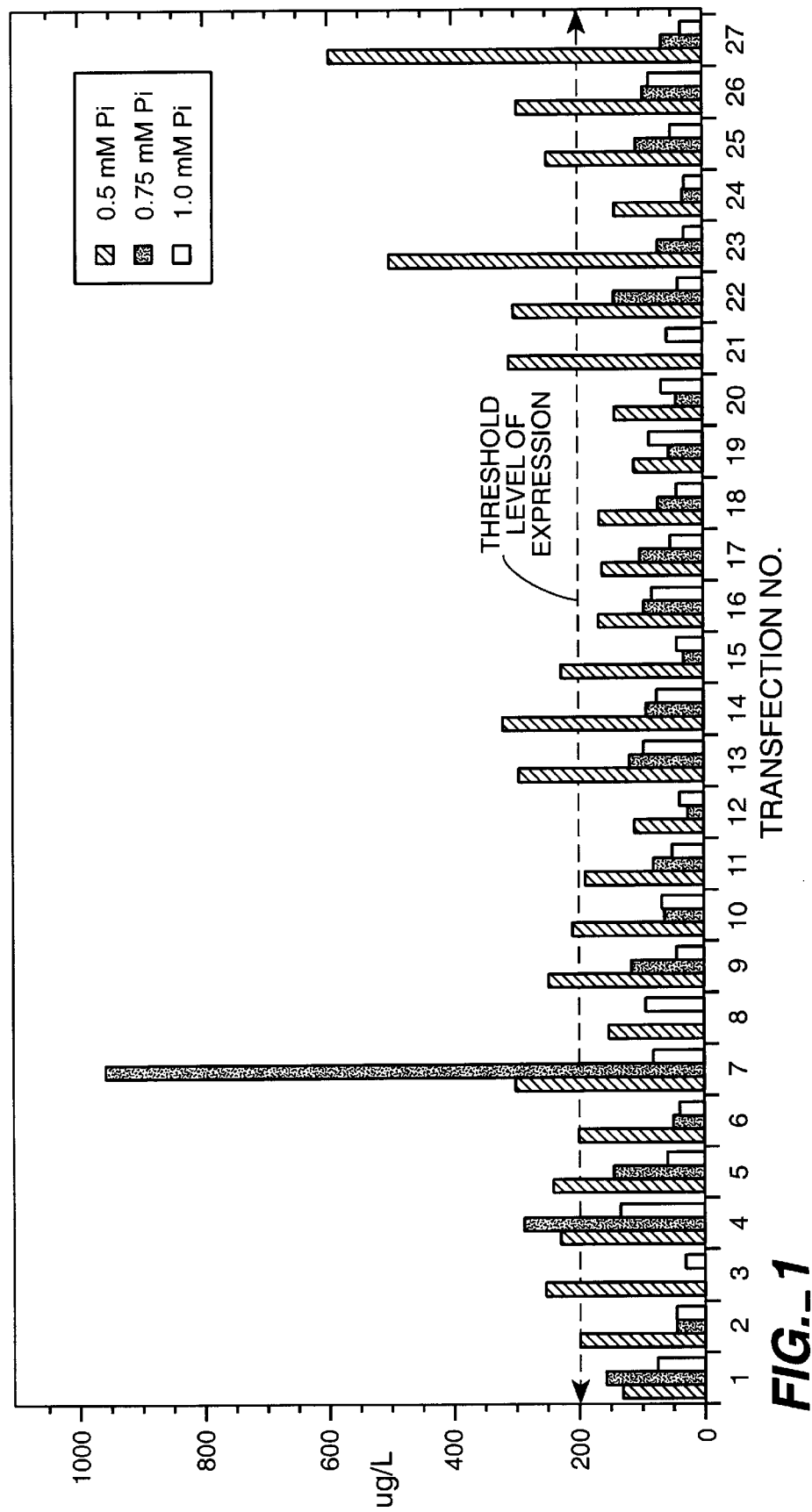
FIG._1

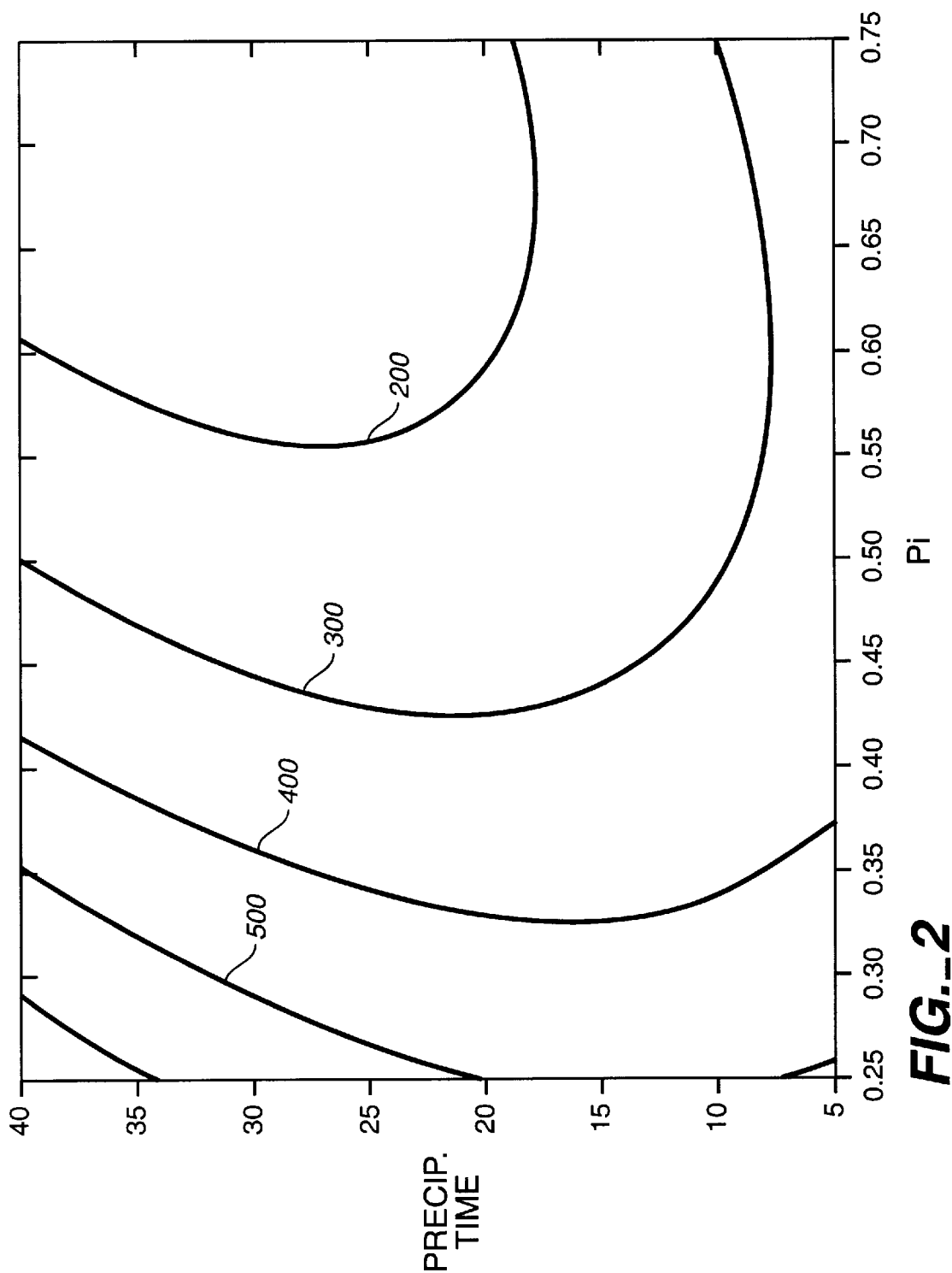
FIG._2

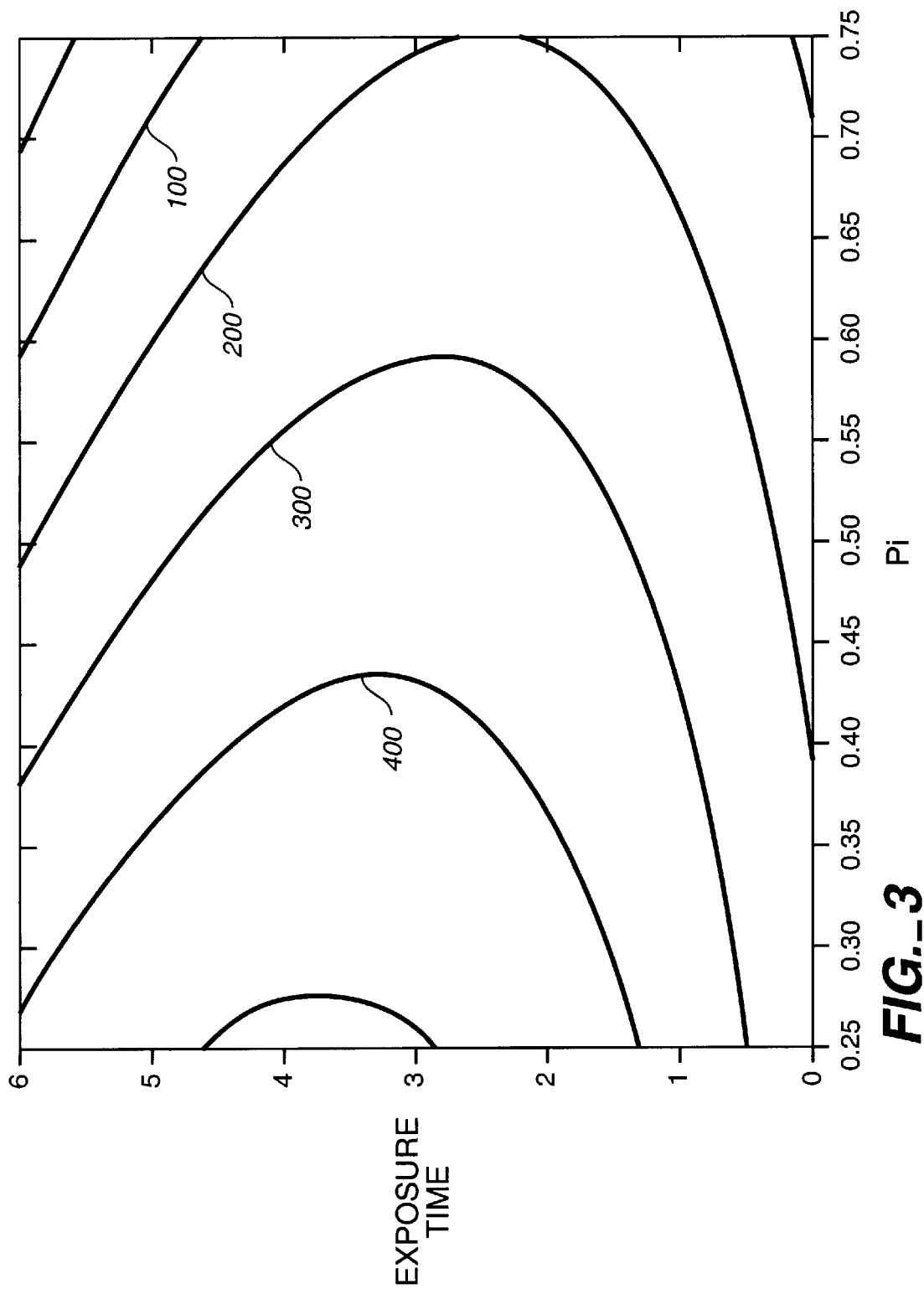
FIG._3

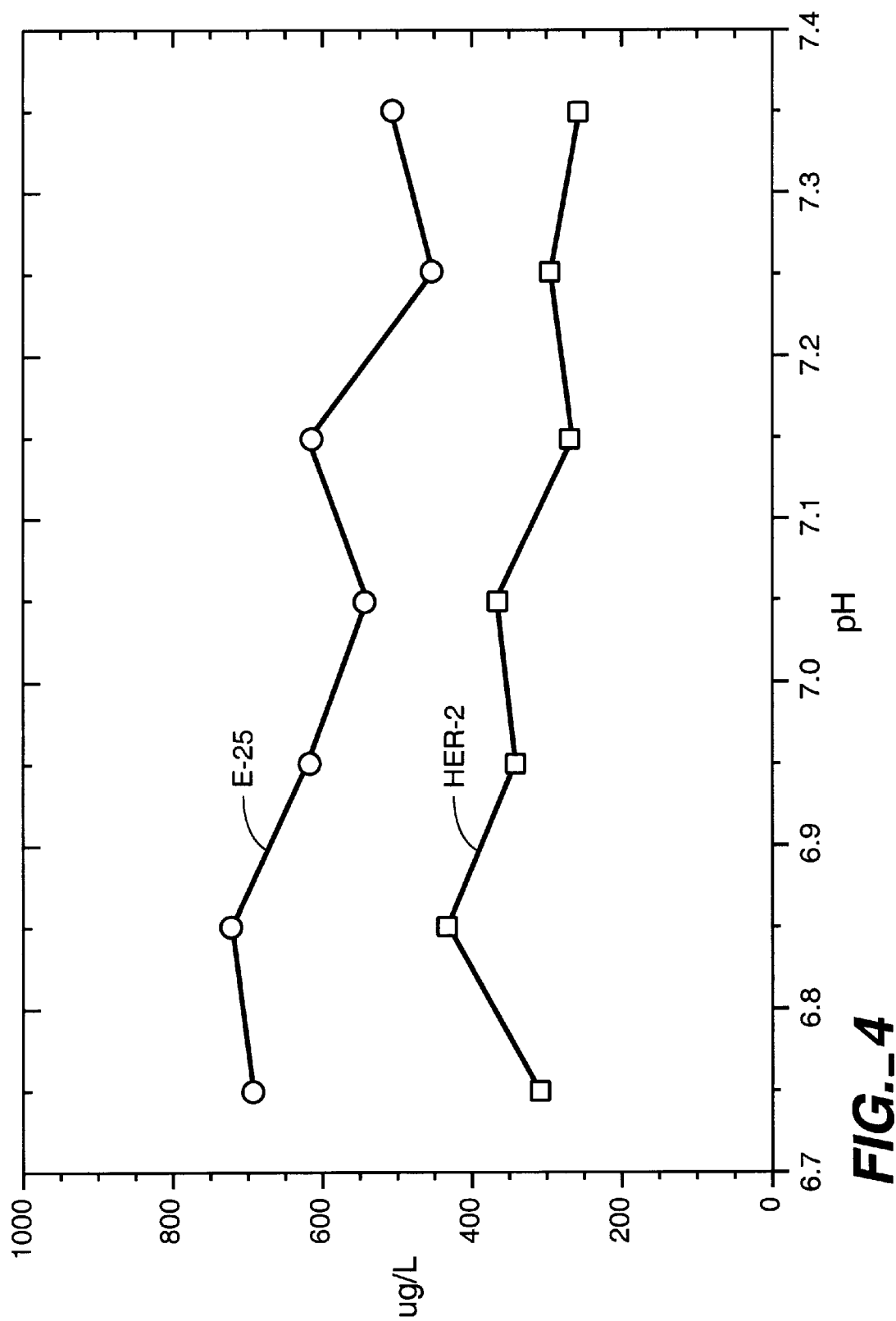
FIG._4

PREPARATION OF CALCIUM PHOSPHATE TRANSFECTACONS

RELATED APPLICATIONS

This application is a non-provisional application filed under 37 CFR 1.53(b)(1), claiming priority under 35 USC 119(e) to provisional application No. 60/113,614 filed Dec. 23, 1998, the contents of which are incorporated herein by reference.

BACKGROUND OF THE INVENTION

1. Field of the Invention

This invention relates to the field of nucleic acid transfection, and more particularly to methods for preparing precipitated complexes of calcium phosphate and nucleic acid, called transfectacons herein, and methods for nucleic acid transfection of eukaryotic cells by calcium phosphate co-precipitation.

2. Related Disclosures

The ability to introduce foreign DNA into eukaryotic host cells is one of the principal tools of recombinant DNA technology. Methods for transfecting eukaryotic host cells with foreign DNA can be broadly grouped into four categories: (1) direct introduction of cloned DNA by microinjection or microparticle bombardment; (2) use of viral vectors; (3) encapsulation within a carrier system; and (4) use of transfecting reagents such as calcium phosphate and diethylaminoethyl (DEAE)-dextran.

Several attempts have been made to improve the transient transfection of mammalian cells using a variety of transfecting reagents that include cationic lipids, DEAE-dextran (or its related analogs), and calcium phosphate (Itani et al., *Gene*, 56: 267–276 (1987); Hofland et al., *Proc. Natl. Acad. Sci.* (*USA*), 93: 7305–7309 (1996); Smyth-Templeton et al., *Nature Biotechnology*, 15: 647–652 (1997); McCutchman and Pagano, *J. Natl. Cancer Inst.*, 41: 351 (1968); Parker and Stark, *J. Virol.*, 31: 360 (1979); Graham et al., *Nature (Lond.)*, 251: 687–691 (1974); Bachetti and Graham, *Proc. Natl. Acad. Sci.* (*USA*), 74(4): 1590–1594 (1977); Wigler et al., *Cell*, 14: 725–731 (1978)). Of the reagents used as facilitators of DNA transfection, calcium phosphate remains the most widely used because of its simplicity and general effectiveness for a wide variety of cell types. Hence, significant attention has been given to improvement of transient transfections using calcium-phosphate/DNA (CaPi/DNA) particles as the transfecting reagent. Hereinafter, the complex formed between a transfecting reagent such as CaPi and the plasmid or nucleic acid that is being introduced into the host cell of choice is referred to as a transfectacon.

The process of introducing nucleic acid sequences into mammalian cells via CaPi transfectacons was first described by Graham and van der Eb, *Virology*, 52: 456–467 (1973). This method, which was modified by Wigler et al., *Cell*, 14: 725–731 (1978) and by Chen and Okayama, *Mol. Cell. Biol.*, 7: 2745–2752 (1987), is based on the formation of small insoluble CaPi transfectacons that attach to the cell surface and are subsequently transported into the cytoplasm via endocytosis (Loyter et al., *Proc. Natl. Acad. Sci.* (*USA*), 79: 422–426 (1982); Loyter et al., *Exp. Cell Res.*, 139: 223–234 (1982)). Once internalized, these nucleic acids are transported to the nucleus by means of an endosomal-lysosomal vesicular transport system (Orrantia et al., *Somat. Cell Mol. Gen.*, 16: 305–310 (1990); Orrantia et al., *Exper. Cell Res.*, 190: 170–174 (1990); Coonrod et al., *Gene Therapy*, 4: 1313–1321 (1997)).

The most widely used protocol for CaPi/DNA transient transfection of mammalian cells (Sambrook et al., *Molecular Cloning: A Laboratory Manual* 2nd Ed. (Cold Spring Harbor Laboratory Press: Cold Spring Harbor, N.Y., 1989)) involves the formation of CaPi transfectacons at pH 7.05 and standard concentrations of $CaCl_2$, $Na_2HPO_4$, and DNA, which are incubated for 20–30 minutes at room temperature. Although this protocol is easily implemented in most laboratories for the generation of both stable and transient transfections, there are several problems that are experienced when using this method (Sambrook et al., supra): 1) this protocol is highly variable from transfection to transfection; 2) scaling this process is very difficult due to the lack of specifications for the variables in the reactions; and 3) the titers achieved are low compared to other transfection systems.

In an attempt to improve CaPi transfections of mammalian cells, particular attention has been given to various aspects of the transfectacon formation both as a separate step prior to its addition to cells and as a simultaneous step wherein the transfectacons are formed in the presence of adherent cells or suspension-adapted cells (Song and Lahiri, *Nucleic Acids Res.*, 23(17): 3609–3611 (1995); Jordan et al., *Nucleic Acids Res.*, 24 (4): 596–601 (1996); Jordan et al., *Cytotechnology*, 26: 39–47 (1998)). The formation of transfection-competent CaPi transfectacons has been shown to be sensitive to changes in pH of less than 0.1 pH units (Chen and Okayama, supra; O'Mahoney and Adams, *DNA Cell Biol.*, 13: 1227–1232 (1994); Jordan et al., *Nucleic Acids Res.*, supra). The basis of this sensitivity is not completely understood, but a recent report suggests that the pH of the precipitation reaction affects the flocculation coefficient and the zeta potential for the CaPi transfectacons (Yang and Yang, *Drug Delivery*, 3: 173–179 (1996); Yang and Yang, *Drug Delivery*, 3: 181–186 (1996)), under the standard concentrations for the reactants used in these studies.

In other investigations designed to examine the significance of the concentrations of the reactants in the co-precipitation reactions, improvements to the existing protocol were achieved (Chen and Okayama, supra; Song and Lahiri, supra; Jordan et al., *Nucleic Acids Res.*, supra; Wilson et al., *Anal. Biol.* 226: 212–220 (1995)). In these experiments, one variable was changed between each experiment while the remaining variables were held constant, which makes assessment of the interactions amongst variables very difficult.

Many investigations into the length of time required for improving co-precipitation of CaPi transfectacons have been conducted. These studies show that at standard or near-standard concentrations of calcium, phosphate, and DNA, shorter precipitation times have resulted in higher transfection efficiencies and/or expression titers relative to transfections that followed the standard protocol (O'Mahoney and Adams, supra; Jordan et al., *Nucleic Acids Res.*, supra; Coonrod et al., supra). It has been proposed that these shorter precipitation times yield CaPi transfectacons that are more easily taken up by cells, presumably due to smaller particle size of the precipitate. See also U.S. Pat. Nos. 5,633,156; 5,593,875; 5,686,263; and 5,484,720, which describe the incubation of particles so that they grow to an average length of up to about 300 nm. To date, accurate measurement of these particles and correlation between particle size and transfection efficiency or protein expression have not been reported (Parasrampuria, *BioPharm.*, 3:38–45 (1998)).

Additionally, throughout the literature, standard or near standard co-precipitation conditions are not very robust in that they yield highly variable titers between transfections that are performed on different days (Sambrook et al., supra).

Since the original and modified protocols yield relatively low transfection efficiencies and expression in experiments geared towards transient or stable transfections, there is still a need for an improved and robust method of calcium phosphate transfection and improved titers for recombinant proteins. In addition, there is a need for methods of calcium phosphate transfection in suspension culture, particularly in the area of large-scale suspension culture, which is currently lacking.

SUMMARY OF THE INVENTION

Accordingly, the invention provides a process for preparing transfectacons of calcium phosphate and a desired nucleic acid comprising:
a) admixing calcium divalent cation, phosphate multivalent anion, and the desired nucleic acid to form a precipitation mixture, wherein the precipitation mixture comprises an initial phosphate anion concentration of about 0.2 to 0.5 mM; and
b) incubating the precipitation mixture for about 10 to 60 minutes to form transfectacons comprising calcium phosphate and the desired nucleic acid.

Also provided are transfectacons prepared by the above process.

In a further embodiment, the invention provides a process for delivering desired nucleic acid to tissue or cells comprising introducing to the tissue or cells the above transfectacons.

In yet another embodiment, the invention supplies a process for introducing a desired nucleic acid into a eukaryotic host cell, which process comprises:
a) admixing calcium divalent cation, phosphate multivalent anion, and the desired nucleic acid to form a precipitation mixture, wherein the precipitation mixture comprises an initial phosphate anion concentration of about 0.2 to 0.5 mM;
b) incubating the precipitation mixture for about 10 to 60 minutes to form transfectacons comprising calcium phosphate and the desired nucleic acid;
c) diluting the precipitation mixture and admixing it with a eukaryotic host cell lacking a cell wall to form a transfection mixture; and
d) incubating the transfection mixture to allow the eukaryotic host cell to take up the transfectacons to form a transfected cell.

Despite the fact that co-precipitation of CaPi and nucleic acid has been used for over 20 years for introducing nucleic acids into mammalian cells, protein expression and transfection efficiencies achieved in CaPi transfections are highly variable. Further, the preferred precipitation time of approximately 1 minute determined in the studies herein does not lend itself easily to larger volumes due to liquid handling limitations. This invention is based on the discovery that the major factors affecting the transient expression of proteins in this type of transfection are the phosphate concentration in the reaction and the length of precipitation time, and that those variables are interactive, while the concentration of nucleic acid in these reactions affects expression to a lesser extent. The concentration of calcium in these reactions was not a factor that significantly affected transient titers.

This new set of conditions for CaPi transfectacon formation provides a robust process that generates significant increases in protein titers, results in an increase in the reproducibility of protein expression, and is more amenable to scaling into a larger process due to providing an increased period of time to control the co-precipitation reaction. Also, unexpectedly the phosphate concentration and length of the co-precipitation reaction involved in the co-precipitation of CaPi and nucleic acid interact to increase resulting titers in transient transfection experiments.

The invention herein provides an improved method of calcium phosphate transfection in both adherent cell cultures and scaled suspension cultures, preferably adherent cell cultures. The methods provided herein are useful for transfection in large-scale suspension cultures, e.g., suspension cultures that are at least about 0.5 liters (L) in volume, preferably about 0.5–50 L.

BRIEF DESCRIPTION OF THE DRAWINGS

FIG. 1 shows the normalized transient expression of anti-HER-2 at 0.5, 0.75, and 1.0 mM phosphate in co-precipitation reactions. Anti-HER-2 expression was measured for 81 individual co-precipitation reactions that contained varying calcium, DNA, and phosphate concentrations with variable precipitation times. The co-precipitation conditions are grouped according to the phosphate concentration in the reactions: 0.5 mM-hashed bars; 0.75 mM-black bars; 1.0 mM-dotted bars. Anti-HER-2 concentrations in harvested cell culture fluid (HCCF) 132 hours post-transfection were measured by Anti-HER-2 ELISA and normalized using triplicate control transfections (125 mM calcium, 0.75 mM phosphate, 25 µg/mL plasmid DNA, and a precipitation time of 1 min.) that were performed in tandem with each set of test transfections. An arbitrary threshold level of expression (200 µg/L) was chosen to evaluate sets of conditions that yielded moderate levels of transient protein expression.

FIG. 2 shows a surface-response curve for anti-HER-2 expression as a function of co-precipitation times and concentration of phosphate in the co-precipitation reaction. Transient transfections were performed according to the outline in the central composite design. The resulting titers 108 hours post-transfection were used to generate a surface-response curve that shows the relationship between concentration of phosphate in co-precipitation reactions and the length of co-precipitation time.

FIG. 3 shows a surface-response curve for anti-HER-2 expression and exposure times. Transient transfections were performed according to the central composite design and the resulting anti-HER-2 titers 108 hours post-transfection used to generate a surface-response curve.

FIG. 4 shows the effect of varying pH in co-precipitation reactions on transient expressions of anti-HER-2 and the anti-IgE antibody E-25. Transfections were performed using the newly-identified levels for the co-precipitation variables (250 mM calcium, 0.25 mM phosphate, 50 µg/mL DNA, and co-precipitation time of 20 minutes) at varying pH. Seven reactions were performed over a range in pH of 6.75–7.35, with an incremental increase of 0.1 pH units. Anti-HER-2 (black squares) and E-25 (black diamonds) titers 132 hours (5.5 days) post-transfection are expressed in µg/L.

DETAILED DESCRIPTION OF THE PREFERRED EMBODIMENTS

Definitions:

As used herein, the term "transfection" is defined as the introduction of an extracellular nucleic acid into a host cell by any means known in the art, including calcium phosphate co-precipitation, viral transduction, liposome fusion, microinjection, microparticle bombardment, electroporation, etc. The terms "uptake of nucleic acid by a host cell", "taking up of nucleic acid by a host cell", "uptake of particles comprising nucleic acid by a host cell", and "taking up of particles comprising nucleic acid by a host cell" denote any process wherein an extracellular nucleic acid, with or without accompanying material, enters a host cell.

As used herein, a "transfectacon" refers to the complex, particles, and/or precipitate formed between a transfection or transfecting reagent (e.g., cationic lipids, commercial polymers, DEAE, CaPi, etc.) and the plasmid or nucleic acid being introduced into the host cell of choice.

As used herein, the terms "nucleic acid-calcium phosphate co-precipitation" and "calcium phosphate co-precipitation" refer to a process wherein nucleic acid, Ca, and $PO_4$ in solution form CaPi transfectacons comprising a complex of hydroxyapatite, which is referred to herein as "calcium phosphate," and nucleic acid. Also included within the definition is the growth of such transfectacons by further precipitation or by aggregation and/or rearrangement of such transfectacons.

As used herein, the term "calcium phosphate transfection" refers to any method of transfecting a host cell wherein calcium phosphate is used to facilitate the uptake of nucleic acid by a host cell.

As used herein, the term "transformation" denotes introducing nucleic acid into a host cell so that the nucleic acid is replicable, either as a chromosomal integrant or as an extrachromosomal element.

As used herein, "multivalent" or "polyvalent" refers to a di-, tri-, or higher valency of an ion, preferably a divalent anion for phosphate.

As used herein, "adherent" cells refers to cells grown as a monolayer, for example, those grown in Dulbecco-modified Eagle medium (DMEM) supplemented with 2% fetal calf serum in an incubator at 35° C. under a 5% CO2 atmosphere.

As used herein, "suspension-adapted cells" refers to cells grown in spinner flasks or bioreactors that are kept in an exponential growth phase, such as by subcultivation with fresh medium every 3 to 6 days. Standard techniques, methods, and equipment for this growth process are reviewed in Lubiniecki, ed., *Large Scale Mammalian Cell Culture Technology* (Marcel Dekker: New York and Basle, 1990).

As used herein, the term "eukaryotic host cell lacking a cell wall" refers to any nucleated cell that has no cell wall in the cell's native state, including all vertebrate cells, such as mammalian cells, avian cells, reptilian cells, amphibian cells, and fish cells, cells of multicellular invertebrate animals, such as insect cells, crustacean cells, and mollusk cells, cells of protozoans, etc., and to any nucleated cell that has had its native cell wall removed or is in a natural or artificially-induced state wherein no cell wall is present, including all plant cells that are capable of forming protoplasts or are capable of being treated to form protoplasts.

As used herein, the term "desired nucleic acid" refers to any desired DNA, RNA or DNA/RNA hybrid, including those contained on a vector such as a plasmid.

As used herein, the term "desired DNA" is defined as any polydeoxynucleotide, including, e.g., double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, plasmid DNA, chromosomal DNA, labeled DNA, such as radiolabeled DNA and fluorochrome-labeled DNA, DNA containing one or more non-naturally occurring species of nucleic acid, etc., that is selected for transfecting a host cell.

As used herein, the term "desired RNA" is defined as any polyribonucleotide, including, e.g., single-stranded RNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently-crosslinked RNA, enzyme-digested RNA, sheared RNA, mRNA, hnRNA, tRNA, including both charged and uncharged tRNA, rRNA, all forms of viral genomic RNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid, etc., that is selected for transfecting a host cell.

As used herein, the terms "desired DNA/RNA hybrid" and "desired hybrid DNA/RNA" are defined as any hybrid nucleic acid comprising one strand of DNA and one strand of RNA wherein the DNA strand and the RNA strand form a species that is at least partially double-stranded, including hybrids wherein the DNA strand is fully complementary or only partially complementary to the RNA strand, hybrids wherein the DNA strand and/or the RNA strand has (have) an uninterrupted phosphodiester backbone, hybrids wherein the DNA strand and/or the RNA strand is (are) composed of two or more fragments, hybrids containing one or more single-stranded portion(s) and one or more double-stranded portion(s), hybrids created by reverse transcription of RNA, hybrids created by transcription of DNA, hybrids created by annealing of complementary or partially-complementary DNA and RNA, covalently cross-linked hybrids, chemically-synthesized hybrids, semi-synthetic hybrids, biosynthetic hybrids, naturally-isolated hybrids, labeled hybrids, such as radiolabeled hybrids and fluorochrome-labeled hybrids, hybrids containing one or more non-naturally occurring species of nucleic acid, etc.

As used herein "polypeptide" or "polypeptide of interest" refers generally to peptides and proteins having more than about ten amino acids. The polypeptides may be "homologous" to the host (i.e., endogenous to the host cell being utilized), or "heterologous," (i.e., foreign to the host cell being utilized), such as a human protein produced by yeast. The polypeptide may be produced as an insoluble aggregate or as a soluble polypeptide in the periplasmic space or cytoplasm of the cell, or in the extracellular medium. The preferred polypeptides herein are eukaryotic, more preferably mammalian, most preferably human.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; cxl-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA) including variants thereof such as glycosylation variants, e.g., T103N,N117Q, KHRR296–299AAAA also known as TNK (U.S. Pat. No. 5,612,029; WO93/24635 published Dec. 9, 1993); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-$\beta$; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The particularly preferred polypeptides of interest herein are t-PA, TNK, VEGF, gp120, anti-HER-2, anti-IgE, anti-CD11a, anti-CD18, DNase, IGF-I, IGF-II, brain IGF-I, growth hormone, relaxin chains, growth hormone releasing factor, insulin chains or pro-insulin, urokinase, immunotoxins, neurotrophins, and antigens. Most particularly preferred mammalian polypeptides include, e.g., anti-HER-2, an antibody to IgE such as E25, t-PA, TNK, DNase, and VEGF.

The term "control sequences" refers to DNA sequences necessary for the expression of an operably linked coding sequence in a particular host organism. The control sequences that are suitable for eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context. The cells herein are generally eukaryotic, preferably mammalian.

As used herein, "tissue" may be any tissue from any source, preferably eukaryotic, and most preferably mammalian.

Modes for Carrying Out the Invention

One of the processes disclosed herein is an improved one for preparing transfectacons of calcium phosphate and a desired nucleic acid, particularly for delivery to target tissues in a drug-delivery or gene-therapy mode. The transfectacons are prepared by admixing calcium divalent cation, phosphate multivalent anion, and the desired nucleic acid to form a precipitation mixture, wherein the precipitation mixture comprises an initial phosphate anion concentration of about 0.2 to 0.5 mM; and incubating the precipitation mixture for about 10 to 60 minutes to form the transfectacons.

In a preferred embodiment, this process further entails a step of diluting the co-precipitation mixture with culture medium and then placing the diluted mixture on cells. Also, preferably the nucleic acid comprises a fragment encoding a polypeptide, preferably a eukaryotic polypeptide, operably linked to one or more control sequences therefor, and the recovered transfectacons are delivered to eukaryotic tissue or cells, more preferably mammalian tissue or cells such as CHO or human cells.

Preferably, the control sequence linked to the nucleic acid encoding the polypeptide is a promoter. Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Polypeptide transcription from vectors in mammalian host cells is controlled, for example, by promoters obtained from the genomes of viruses such as polyoma virus, fowlpox virus (UK 2,211,504 published Jul. 5 1989), adenovirus (such as Adenovirus 2), bovine papilloma virus, avian sarcoma virus, cytomegalovirus, a retrovirus, hepatitis-B virus, and Simian Virus 40 (SV40); from heterologous mammalian promoters, e.g., the actin promoter or an immunoglobulin promoter; and from heat-shock promoters, provided such promoters are compatible with the host cell systems.

Transcription of a DNA encoding a polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the desired coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide. All these nucleic acid elements may be incorporated into the desired nucleic acid herein depending on its ultimate use.

This invention also provides a process for delivering desired nucleic acid to tissue or cells comprising introducing to the tissue or cells the transfectacons prepared as described above. This may be done by any suitable procedure for gene therapy or gene delivery to tissue or cells.

There are a variety of techniques available for introducing transfectacons into viable cells. The techniques vary depending upon whether the nucleic acid is transferred into cultured cells in vitro, or transferred in vivo or ex vivo in the cells of the intended host.

There are two major approaches to getting the nucleic acid (optionally contained in a vector) directly into a patient's cells for gene therapy: in vivo and ex vivo. For in vivo delivery the nucleic acid in the transfectacon is injected directly into the patient, usually at the site where the polypeptide encoded by the nucleic acid is required. For ex vivo treatment, the patient's cells are removed, the nucleic acid in the transfectacon is introduced into these isolated cells and the modified cells are administered to the patient either directly or, for example, encapsulated within porous membranes that are implanted into the patient (see, e.g., U.S. Pat. Nos. 4,892,538 and 5,283,187).

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example; see, e.g., Tonkinson et al. *Cancer Investigation*, 14(1): 54–65 (1996)). In some situations it is desirable to provide the nucleic acid source with an agent that targets the target cells, such as an antibody specific for a cell-surface-membrane protein or the target cell, a ligand for a receptor on the target cell, etc. Where liposomes are employed, proteins that bind to a cell-surface-membrane protein associated with endocytosis may be used for targeting and/or to facilitate uptake, e.g,. capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262: 4429–4432 (1987); and Wagner et al., *Proc. Natl. Acad. Sci. USA*, 87: 3410–3414 (1990). For a review of the currently-known gene marking and gene therapy protocols, see Anderson et al., *Science*, 256: 808–813 (1992). See also WO 93/25673 and the references cited therein, and U.S. Pat. No. 5,681,746.

The desired nucleic acid may also be introduced by transplantation into a mammal of nonautologous cells designed to produce the polypeptide via an implantable device suitable for cellular transplantation (e.g., Thera-Cyte™ bags produced by Baxter). These nonautologous cells are preferably human cells and are preferably modified ex vivo to express or produce the polypeptide. The technology for these implants is described, for example, in U.S. Pat. Nos. 5,421,923; 5,453,278; 5,314,471; 5,344,454; 5,545,223; and 5,549,675. Briefly, an implant assembly, without the cells to be implanted, may be implanted within a host. Preferably, the assembly is allowed to prevascularize. After vascularization of the implant assembly, the cells to be implanted, which are transfected with the transfectacons herein, are then added to the assembly.

Transfectacons are typically used for the transfer of nucleic acid into mammalian cells in vitro. A host cell can be exposed in vitro or ex vivo to the transfectacons in at least three ways: (1) forming the transfectacons (DNA-calcium phosphate co-precipitate), and then diluting the transfectacons and contacting them with the host cell in a single step by admixing the transfectacons with a host cell culture; (2) forming the transfectacons, diluting the transfectacons, and then admixing the diluted transfectacons with a host cell culture; and (3) forming the transfectacons in a host cell culture, and then diluting the host cell culture.

I. Simultaneous Dilution of Transfectacon and Exposure to Host Cell a. Host Cell Preparation Any eukaryotic host cell lacking a cell wall can be used in the methods of the invention. Preferred for use herein are mammalian cells. Examples of useful mammalian host cell lines include monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 (1977)); baby hamster kidney cells (BHK, ATCC CCL 10); Chinese hamster ovary cells/-DHFR (CHO, Urlaub and Chasin, *Proc. Natl. Acad. Sci. USA*, 77: 4216 (1980)); mouse sertoli cells (TM4, Mather, *Biol. Reprod.*, 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 (1982)); MRC 5 cells; FS4 cells; and a human hepatoma cell line (Hep G2).

The mammalian host cell of choice can be cultured by any method known in art, such as, e.g., growing the cells as a monolayer with Dulbecco-modified Eagle medium (DMEM) supplemented with 10% calf serum in an incubator at 35° C. under a 5% $CO_2$ atmosphere. Other procedures can be used for particular cell types. For example, Drosophila cell lines can be grown as described by Di Nocera and Dawid, *Proc. Natl. Acad. Sci. USA*, 80: 7095–7098 (1983) and fish cell lines can be grown as described by Araki et al., *Bull. Natl. Res. Inst. Aquaculture*, 20: 1–9 (1991).

Alternatively, a suspension cell culture can be used. Cells in suspension can be grown in spinner flasks, ranging in volume from 100 milliliters (ml) to 10 liters (L) or in bioreactors ranging in volume from 0.5 L to 10,000 L. Cells in a suspension culture are kept in an exponential growth phase that can be achieved by several methods known in the art, the most common of which is subcultivation with fresh medium every 3 to 6 days. Standard techniques, methods, and equipment are reviewed in Lubiniecki, supra.

In the case of plant cell hosts, the plant cell protoplast cultures suitable for use herein can be prepared according to the method of Lichtenstein and Draper, "Genetic Engineering of Plants", in *DNA Cloning Volume III: A Practical Approach*, Glover, ed, (IRL Press, 1985), pp.67–119.

b. DNA Preparation

Any desired DNA for use in the methods of the invention can be prepared by a variety of methods known in the art. These methods include, but are not limited to, chemical synthesis by any of the methods described in Engels et al., *Angew. Chem. Int. Ed. Engl.*, 28: 716–734 (1989), the entire disclosure of which is incorporated herein by reference, such as the triester, phosphite, phosphoramidite, and H-phosphonate methods. Alternatively, the desired DNA sequences can be obtained from existing clones or, if none are available, by screening DNA libraries and constructing the desired DNA sequences from the library clones.

Suitable quantities of DNA template for use herein can be produced by amplifying the DNA in well-known cloning vectors and hosts, such as plasmid vectors carrying the pBR322 origin of replication for autonomous replication in most Gram-negative bacterial hosts, plasmid vectors carrying the pC194 (Ehrlich, *Proc. Natl. Acad. Sci. USA*, 75: 1433–1436 (1978)) origin of replication for autonomous replication in Bacillus and some other Gram-positive bacterial hosts, or 2-micron circle (2μ plasmid) vectors carrying an origin of replication for autonomous replication in most yeast hosts.

Alternatively, the DNA template can be amplified by polymerase chain reaction (PCR) as described by Saiki et al., *Science*, 230: 1350 (1985), Mullis et al., *Cold Spring Harbor Symp. Quant. Biol.*, 51: 263 (1986), Mullis and Faloona, *Methods Enzymol.*, 155: 335 (1987), and Saiki et al., *Science*, 239: 487 (1988).

c. RNA Preparation

Any desired RNA for use in the methods of the invention can be prepared by a variety of methods known in the art. These methods include, but are not limited to, chemical synthesis of RNA, and in vitro translation of a DNA template as described generally in *Current Protocols in Molecular Biology* (Wiley Interscience: New York, 1990). Alternatively, the desired RNA can be isolated from total cellular RNA extracted from a host cell culture. Total cellular RNA can be isolated from the host cell culture by any method known in the art such as, in the case of RNA produced in mammalian host cells, the methods described by Favaloro et al., *Methods Enzymol.*, 65: 718 (1980); Stallcup and Washington, *J. Biol. Chem.*, 258: 2802 (1983); Birnboim, *Nucleic Acids Res.*, 16: 1487 (1988); Gilsin et al., *Biochemistry*, 13: 2633 (1974); Ullrich et al., *Science*, 196: 1313 (1977); Strohman et al., *Cell*, 10: 265 (1977); and MacDonald et al., *Methods Enzymol.*, 152: 219 (1987).

If the desired RNA is a polyadenylated mRNA fraction of total cellular RNA, the polyadenylated mRNA can be separated from the bulk of cellular RNA by affinity chromatography on oligodeoxythymidylate (oligo(dT))-cellulose columns using any method known in the art, such as the method of Edmonds et al., *Proc. Natl. Acad. Sci., USA*, 68: 1336 (1971) or the method of Aviv and Leder, Proc. Natl. Acad. Sci., USA, 69: 1408 (1972).

If the size of the desired mRNA is known, the mRNA preparation can be further purified for mRNA molecules of the particular size by agarose gel electrophoresis of RNA in the presence of methylmercuric hydroxide as described in Lemischka et al., *J. Mol. Biol.*, 151: 101 (1981) or fractionation of RNA by sucrose density gradient centrifugation in the presence of methylmercuric hydroxide as described by Schweinfest et al., *Proc. Natl. Acad. Sci., USA*, 79: 4997 (1982).

In addition, the desired RNA can be obtained from the recombinant or non-recombinant genome of an RNA virus, including single-stranded RNA viruses, such as retroviruses, tobacco mosaic viruses, influenza viruses, Newcastle disease virus, and double-stranded RNA viruses such as rotaviruses and rice dwarf virus. The desired RNA can be isolated by growing up the chosen RNA virus in a suitable host cell culture, harvesting the viral particles, and then extracting the desired RNA from the viral particles. For example, the genomic RNA of Moloney's murine leukemia virus can be obtained according to the method of Schwartzberg et al., *Cell*, 37: 1043 (1984).

d. DNA/RNA Hybrid Preparation

The DNA/RNA hybrids suitable for use in the methods of the invention can be prepared by any method known in the art. In one embodiment, the DNA strand or DNA fragments are produced as described in Section I(b) above, the RNA strand or fragments are produced as described in Section I(c) above, and the DNA and RNA strands or fragments are admixed together and allowed to anneal. In another embodiment, the DNA/RNA hybrid can be produced by obtaining the desired DNA strand as described above, using the DNA strand as a template to drive synthesis of the complementary RNA strand by a DNA-directed RNA polymerase, and harvesting the DNA/RNA hybrid upon completion of the transcription reaction. Alternatively, the DNA/RNA hybrid can be prepared by obtaining the desired RNA strand as described above, using the RNA strand as a template to drive synthesis of the complementary DNA strand by a RNA-directed DNA polymerase, and harvesting the DNA/RNA hybrid upon completion of the reverse-transcription reaction.

e. Procedure for Calcium Phosphate Transfection

The invention encompasses any method for introducing a desired nucleic acid into a eukaryotic host cell wherein the desired nucleic acid, Ca, and $PO_4$ are admixed to form a precipitation mixture, wherein the initial concentration of the phosphate anion in the mixture ranges from about 0.2 to 0.5 mM, the precipitation mixture is incubated to form transfectacons comprising calcium phosphate and the desired nucleic acid for a period of time of about 10 to 60 minutes, the precipitation mixture is simultaneously diluted and admixed with a eukaryotic host cell lacking a cell wall to form a transfection mixture, and the transfection mixture is incubated to allow the host cell to take up the transfectacons to form a transfected cell.

1. Formation of the Precipitation Mixture

Ca, $PO_4$, and the desired nucleic acid can be admixed in any order to form a precipitation mixture wherein the nucleic acid co-precipitates with calcium phosphate. In one embodiment, the number of transfectacons comprising nucleic acid and calcium phosphate formed in the precipitation mixture are maximized by admixing the nucleic acid with the precipitation mixture before or simultaneously with the admixture of Ca and $PO_4$. The nucleic acid can be suspended in a buffer lacking both Ca and $PO_4$ and then Ca and $PO_4$ Can be consecutively or simultaneously admixed with the nucleic acid suspension. Alternatively, the nucleic acid can be suspended in a buffer containing Ca or $PO_4$ and then the appropriate counter-ion can be admixed with the nucleic acid suspension to initiate co-precipitation.

It has been found that the phosphate concentration ($PO_4$ concentration) at a selected range provides far superior properties. $PO_4$ is present at an initial concentration of about 0.2 mM to about 0.5 mM and preferably about 0.2–0.3 mM, and most preferably about 0.25 mM. At a given $PO_4$ concentration, a higher Ca concentration can result in formation of transfectacons with greater speed and frequency. The Ca concentration, $PO_4$ concentration, pH, and temperature of the precipitation mixture are selected to provide a calcium phosphate solubility well below the actual Ca concentration and $PO_4$ concentration in the mixture, thus providing a supersaturation of Ca and $PO_4$ ions that drives co-precipitation of calcium phosphate and nucleic acid.

In the precipitation mixture, Ca can be present at an initial concentration of about 125 mM to about 375 mM, and preferably about 180 mM to about 300 mM, more preferably about 180 to 270 mM, and most preferably about 230 to 270 mM. The nucleic acid concentration varies, for example, with the Ca or $PO_4$ concentration in the precipitation mixture and may be about 25 to 100 µg/ml, preferably about 30 to 100 µg/ml, more preferably about 40 to 60 µg/ml, and most preferably about 45 to 55 µg/ml.

Due to volumetric constraints in large-scale suspension culture transfection, it is desirable to increase the Ca concentration in the suspension culture prior to inoculation with the precipitation mixture. Under these circumstances, it is advantageous to reduce the Ca concentration in the precipitation mixture to compensate for the increased Ca concentration in the suspension culture.

The pH of the precipitation mixture can be about 6.8 to about 7.6, and is preferably about 7.05. The temperature of the precipitation mixture can be about 0° C. to about 37° C., preferably about 20° C. to about 37° C., and more preferably about 20° C. to about 25° C. However, any precipitation mixture incubation temperature, including any temperature outside of the foregoing temperature ranges, that combines with the other reaction parameters to produce the desired rate of transfectacon formation is contemplated for use in the methods of the invention.

Any pH buffer that is effective at a pH range encompassing the desired pH for the precipitation mixture can be used to suspend the reactants in the precipitation mixture. Buffers that are suitable for use herein include appropriate concentrations of N-3-hydroxyethylpiperazine-N'-3-ethanesulfonic acid (HEPES)-buffered saline, such as 25 mM HEPES and 140 mM NaCl, and appropriate concentrations of N,N-bis (3-hydroxyethyl)-3-aminoethanesulfonic acid (BES)-buffered saline, such as 25 mM BES and 140 mM NaCl.

In general, the precipitation mixture is incubated for a period of time ranging from about 10 to 60 minutes, preferably about 15 to 30 minutes, to maximize the properties desired herein. It is noted that the particular initial concentration of phosphate chosen and the particular incubation time chosen for the precipitation mixture are interrelated. The longer the incubation time, generally the lower the concentration of phosphate employed initially in the precipitation reaction.

As to the size of the transfectacons ultimately obtained, although the transfectacons can be grown to any reasonable size, preferably they are allowed to grow to an average length of less than about 300 nm, most preferably less than about 250 nm.

2. Formation of the Transfection Mixture

After transfectacons comprising calcium phosphate and the desired nucleic acid have been incubated in the precipitation mixture for the required period of time, the precipitation mixture is simultaneously diluted and admixed with a eukaryotic host cell lacking a cell wall to form a transfection mixture. The eukaryotic cell is obtained in the form of an adherent cell culture or a suspension cell culture as described in section I(a) above. As provided herein, the precipitation mixture is diluted by admixture with the host cell culture such that the growth rate of the transfectacons in the transfection mixture is substantially lowered, compared to the growth rate of the transfectacons in the precipitation mixture, without allowing re-solvation of the transfectacons, thereby maximizing the exposure of host cells to the transfectacons.

Exposure of the cells to the transfectacons takes place generally about 3 hours to about 24 hours, more preferably about 3 hours to about 12 hours.

In a preferred embodiment using a suspension cell culture, the precipitation and dilution steps are accomplished in an automated system wherein nucleic acid, Ca, and $PO_4$ are fed into an intake pipe that empties into the culture vessel. The nucleic acid, Ca, and $PO_4$ can be fed into the intake pipe in any convenient order. Preferably, the nucleic acid is fed into the intake pipe upstream of the initial point of calcium phosphate precipitate formation. Alternatively, the nucleic acid, Ca, and $PO_4$ are fed into the intake pipe at approximately the same point. In one embodiment, a solution containing the nucleic acid and one of the two ions and a solution containing the counter-ion are fed through separate tube lines that merge into the intake pipe. The flow rate through the intake pipe and the intake pipe length can be regulated to achieve the desired incubation period for nucleic acid-calcium phosphate co-precipitation within the intake pipe. Preferably, the suspension culture is agitated to maximize the contact between host cells and transfectacons of calcium phosphate and nucleic acid.

The methods of the invention can be used to transfect cells in a suspension culture of any size. Preferably, the methods of the invention are used for transfection of suspension cultures comprising a total volume of at least about 0.5 liter, and more preferably comprising a total volume of at least about 0.5–50 liters.

The desired cell density for transfection in suspension culture can be achieved, e.g., by growing a defined volume of the seed culture to the particular cell density. Alternatively, cells from the seed culture are recovered by filtration and/or centrifugation and resuspended at the desired density. In another embodiment, the desired cell density is achieved by dilution of the seed culture.

The cell density for transfection in suspension culture can be about 0.2% to about 5% packed cell volume (PCV). However, the invention also encompasses the use of higher or lower cell densities that provide acceptable levels of transfection in suspension culture. For example, the invention can be practiced by concentrating cells from a bioreactor to obtain a high-density cell slurry, and then admixing the precipitation mixture with the cell slurry. In one embodiment, a cell density of greater than about $10^8$ cells/ml is used. In another embodiment, a cell density of about $10^8$ cells/ml to about $10^9$ cells/ml is used. A concentrated slurry can be obtained by pumping cell suspension from a bioreactor into a semi-continuous aseptic centrifuge, such as the Hereaus Sepatech Contifuge™ 1517RS (1994 Hereaus Instruments Catalog No. 75003571, Hereaus Instruments Gmbh, D63405, Hanau, Germany) and centrifuging the cell suspension at about 500×g to about 6,000×g, and preferably about 5,300×g, to entrap the cells in an aseptic rotor bowl. Depending on the cell density of the bioreactor cell culture, up to about 100 liters of suspension culture can be harvested in the centrifuge rotor bowl. Subsequently, the high-density cell slurry is removed from the bowl and admixed with the calcium phosphate transfectacon to form the transfection mixture. In one embodiment, the high-density cell slurry is admixed with the calcium phosphate transfectacon in an intake pipe to form the transfection mixture in-line prior to entering the bioreactor. Alternatively, the calcium phosphate transfectacon and high-density cell slurry can be separately introduced into the bioreactor through feeding and inoculation ports, respectively. Also provided herein are embodiments in which the cell concentration in the high-density cell slurry is adjusted, e.g., by addition of fresh growth medium, to reach the most preferred concentration for transfection prior to the formation of the transfection mixture. It will be appreciated that the useful cell concentrations for transfection of a particular host cell can easily be determined with routine testing.

In another embodiment using a suspension cell culture, the Ca concentration in the suspension culture is increased prior to inoculation with the precipitation mixture as described above in Section I(e)(1). In a preferred embodiment, the Ca concentration in the suspension culture is raised to about 7.5 mM prior to inoculation with the precipitation mixture.

If it is desired that the transfectacon growth rate be substantially reduced, this can be accomplished by the addition of serum or serum protein, such as bovine serum albumin, to the transfection mixture. Protein, like nucleic acid, associates strongly with the calcium phosphate transfectacon surface and thereby impedes transfectacon growth. In one embodiment, the transfection mixture contains about 2% to about 10% serum, such as fetal calf serum. In another embodiment, the transfection mixture contains about 0.2 grams per liter (g/L) to about 4 g/L serum albumin, such as bovine serum albumin.

The pH and temperature of the transfection mixture are maintained at physiological levels tolerated by the host cells. In the case of mammalian host cells, it is desirable to maintain the pH in the range of about 6.0 to about 8.0, and preferably about 7.2 to about 7.5, and the temperature in the range of about 15° C. to about 39° C., and preferably about 32° C. to about 37° C. Similarly, the transfection mixture is incubated for a period of time that is easily adjusted to the most preferred range for the particular host cell.

In the case of transfection in a suspension cell culture, it is possible to regulate precisely the pH, Ca concentration, $PO_4$ concentration, and temperature such that the solubility of the transfectacons comprising calcium phosphate and the desired nucleic acid is as low as possible without permitting re-solvation of the transfectacons.

Calcium phosphate transfectacons are toxic to some host cells. Accordingly, it can be advantageous to dissolve the transfectacons after the desired incubation period for transfection. The calcium phosphate transfectacon in the transfection mixture can be dissolved, e.g., by lowering the pH and/or lowering the Ca concentration in the transfection mixture. The Ca concentration can be conveniently lowered by adding fresh culture medium to the transfection mixture.

In one suspension culture embodiment, the transfection mixture is incubated for about 3 hours to about 24 hours, and preferably about 3 hours to about 12 hours, and then diluted with about 1 volume to about 500 volumes of cell culture medium and incubated for about 1 day to about 14 days.

For some host cells, an improved rate of transfection is obtained by shocking the cells containing the transfectacons with glycerol or dimethylsulfoxide (DMSO) at the end of the exposure of cells to transfection. Typically, the transfection mixture is exposed to glycerol at a concentration of about 10–20% volume:volume for about 30 seconds to about 3 minutes, depending on the particular host cell, and then the glycerol is removed and the cells are incubated in fresh medium for about 1 to 6 days. Alternatively, following transfection the host cells can be cultured in fresh medium for the desired time period without a glycerol shock.

II. Dilution of Transfectacon Followed by Exposure to the Host Cell

The invention also encompasses any method for introducing a desired nucleic acid into a eukaryotic host cell wherein the desired nucleic acid, Ca, and $PO_4$ are admixed to form a co-precipitation mixture, the precipitation mixture is incubated to form transfectacons comprising calcium phosphate and the desired nucleic acid, the precipitation mixture is diluted to form a diluted precipitation mixture, the diluted precipitation mixture is admixed with a eukaryotic host cell lacking a cell wall to form a transfection mixture wherein the transfectacons are capable of growth at a rate that is substantially lower than the rate at which the transfectacons grew in the precipitation mixture, and the transfection mixture is incubated to allow the host cell to take up the transfectacons to form a transfected cell.

a. Formation of the Precipitation Mixture

The precipitation mixture is obtained and incubated as described in Section I(e)(1) above. After the desired calcium phosphate transfectacon is formed, the precipitation mixture can be diluted by any convenient means, e.g., by adding an appropriate buffer or by adding the cell culture medium to be used in transfection. Buffers and media suitable for use herein are described in Sections I(a) and I(e)(1) above. The diluent is added to the precipitation mixture in an amount sufficient to reduce the rate of calcium phosphate transfectacon growth but not allow re-solvation of such transfectacons in the resulting diluted precipitation mixture.

Until it is admixed with a host cell to form a transfection mixture, the diluted precipitation mixture is maintained under conditions that permit continued but slow growth of the calcium phosphate transfectacons. Suitable conditions for obtaining a slow transfectacon growth rate are set forth in the description of the transfection mixture in Section I(e)(2) above.

b. Formation of Transfection Mixture

As provided herein, the diluted precipitation mixture is admixed with a eukaryotic host cell lacking a cell wall to form a transfection mixture wherein the CaPi transfectacons will grow at a substantially lower rate than the transfectacon growth rate in the precipitation mixture. The eukaryotic cell is obtained in the form of an adherent cell culture or a suspension cell culture as described in Section I(a) above, and the diluted precipitation mixture can be admixed with the cell culture to form a transfection mixture as described in Section I(e)(2) above.

The dilution of the transfectacons in the diluted precipitation mixture and the dilution of the transfectacons in the transfection mixture are chosen such that the overall dilution substantially lowers the transfectacon growth rate without permitting the transfectacons to dissolve. In a preferred embodiment, the overall dilution provides an initial Ca concentration in the transfection mixture that is at least ten-fold lower than the initial Ca concentration in the precipitation mixture.

Alternatively, the percentage of the overall dilution that occurs in the formation of the diluted precipitation mixture and the percentage of the overall dilution that occurs in the formation of the transfection mixture can be varied according to the length of time between the two steps. A short time interval would permit the use of a smaller dilution in the diluted precipitation mixture, whereas a longer time interval would necessitate the use of a larger dilution in the diluted precipitation mixture to prevent undue loss of transfection activity.

Preferably, the diluted precipitation mixture is immediately admixed with host cells to maximize the host cells' exposure to the calcium phosphate transfectacons. However, the invention also encompasses embodiments wherein the diluted precipitation mixture is maintained for any period of time before admixture with the host cells provided that the diluted precipitation mixture retains some ability to transfect the host cells at the time the transfection mixture is formed.

In a preferred embodiment using a suspension cell culture, the precipitation and dilution steps are accomplished in an automated system wherein nucleic acid, Ca, and $PO_4$ feed into an intake pipe that allows nucleic acid-calcium phosphate co-precipitation to occur, diluent feeds into the precipitation mixture through another intake pipe at some point downstream of the nucleic acid, Ca, and $PO_4$ intake, and thereafter the diluted precipitation mixture empties into the culture vessel. The nucleic acid, Ca, and $PO_4$ can be fed into the intake pipe in any convenient order as described in Section I(e) (2) above. The flow rate through the intake pipe that carries the precipitation mixture and the downstream positioning of the diluent intake pipe and the culture vessel entry port can be adjusted to achieve the desired incubation period for the precipitation mixture and the desired delay between dilution of the precipitation mixture and admixture with the host cells in the culture vessel. Preferably, the suspension culture is agitated to maximize the contact between host cells and transfectacons of calcium phosphate and nucleic acid.

After it is formed, the transfection mixture can be incubated under the conditions described in Section I(e)(2) above.

III. Formation of Transfectacon in Host Cell Culture

The invention also encompasses any method for introducing a desired nucleic acid into a eukaryotic host cell wherein Ca, $PO_4$, nucleic acid, and a eukaryotic host cell lacking a cell wall are admixed to form a CaPi transfectacon suspension, the precipitation mixture is incubated to form transfectacons comprising calcium phosphate and the desired nucleic acid, the precipitation mixture is diluted to form a transfection mixture wherein the transfectacons are capable of growth at a rate that is substantially lower than the rate at which the transfectacons grew in the precipitation mixture, and the transfection mixture is incubated to allow the host cell to take up the transfectacons to form a transfected cell.

a. Formation of the CaPi Transfectacons

A suitable host cell culture can be obtained as described in Section I(a) above. The growth medium is removed from the cells, and the cells are exposed to appropriate concentrations of nucleic acid, Ca, and $PO_4$, described in Section I(e) (1) above, to form a CaPi transfectacon. It will be appreciated that the order of admixing nucleic acid, Ca, and $PO_4$ is not important for practicing the invention. The cells can be contacted with or suspended in a mixture containing any of the nucleic acid, Ca, and $PO_4$ components or combination thereof and then admixed with any missing component or components needed to complete the precipitation mixture. Alternatively, the cells can be admixed with all of the nucleic acid, Ca, and $PO_4$ components at once.

In a preferred embodiment, the precipitation mixture is formed by contacting the host cells with an appropriate serum-free growth medium that comprises the desired concentrations of nucleic acid, Ca, and $PO_4$. A medium containing serum or other proteins is undesirable for use in the precipitation mixture because proteins substantially reduce the growth of the calcium phosphate transfectacon.

The precipitation mixture reaction conditions and incubation period are selected to allow formation of transfectacons comprising calcium phosphate and nucleic acid as described in Section I(e)(1) above.

b. Formation of the Transfection Mixture

After a suitable length of time in which the calcium phosphate transfectacons are formed, the precipitation mixture is diluted to form a transfection mixture wherein the transfectacons will grow at a lower rate, preferably a substantially lower rate, than the transfectacon growth rate in the precipitation mixture. In one embodiment, the precipitation mixture is diluted by adding the appropriate serum-supplemented growth medium for the host cells. The resulting transfection mixture is incubated under conditions that allow the host cell to take up the calcium phosphate transfectacons to form a transfected cell. Such procedures are described in Section I(e)(2) above.

Further details of the invention can be found in the following examples, which further define the scope of the invention. All citations throughout the specification and all references cited therein are hereby expressly incorporated by reference in their entirety.

EXAMPLE 1

Materials and Methods

Plasmid Isolation.

The construction and characterization of the plasmids encoding vascular endothelial growth factor (VEGF), DNase, E-(Anti-IgE monoclonal antibody), or anti-HER-2 (α-HER-2 monoclonal antibody) are described in Leung et al., *Science*, 246:1306–1309 (1989); Shak et al., *Proc. Natl. Acad. Sci. USA*, 87: 9188–9192 (1990); Presta et al., *J. Immunol.*, 151: 2623–2632 (1993); Shalaby et al., *J. Exp. Med.*, 175: 217–225 (1992), respectively. Transformation-competent DH5a cells (Gibco-BRL) were transformed according to manufacturer's protocol for the amplification of these ampicillin-resistant (AmpR) plasmids. Overnight cultures of colonies were grown in LB/carbenicillin (50 μg/mL) medium. Plasmid DNA was recovered from these cultures using either a modified alkaline lysis protocol based on that of Birnbolm and Doly, *Nucleic Acids Res.*, 7(6):1513–23 (1979) or the Qiagen Plasmid DNA Purification kit (Qiagen Inc.).

Cell Culture.

DP12, a dihydrofolate reductase positive (DHFR+) Chinese hamster ovarian cell line was used as the recipient cell for all transfection experiments. Cells were maintained in either 500-mL spinners or a solera in which the cells are in the log-phase of growth. A DMEM/F12-based medium supplemented with 1–2% diafiltered FCS (Gibco-BRL) was used for adherent cell cultures and DMEM/F12 without additions was used for cells grown in suspension.

Transfection.

All transfections were conducted according to the following protocol. 24 hrs prior to transfection, 100-mm Petri dishes were seeded for a 70% confluency on the day of transfection (1.0–1.4×10⁶ cells). One hour before transfection, fresh medium was added to plates and plates were returned to the $CO_2$ incubator. All co-precipitation reactions were carried out separately at 20–25° C. Each co-precipitation reaction began with the addition of either 2.5 or 5.0 M $CaCl_2$ to 25–100 μg plasmid DNA dissolved in 50 mM Tris-Cl (pH 7.5). The final calcium concentration for these reactions ranged between 125 and 250 mM. The final volumes of the reactions were adjusted to 0.5 mL by the addition of 0.1×TE (1 mM Tris-Cl, 0.1 mM EDTA). These solutions were added to an equal volume of 2×Hepes-buffered saline (280 mM NaCl, 50 mM Hepes, pH 7.05) with varying $Na_2HPO_4$ concentrations from 0.5 to 2.0 mM. For transfections that tested the effect of pH in co-precipitation reactions on resulting titers of transiently-expressed proteins, the pH of the 2×Hepes buffer (0.5 mM $Na_2HPO_4$) ranged from 6.75 to 7.35 in 0.1 pH units. Co-precipitation reactions were allowed to proceed for the specified time, after which reactions were diluted 1:5 with fresh medium, then added directly to plates that contained 5 mL of medium, thereby generating a 10×dilution of the precipitation reaction. Plates were returned to the $CO_2$ incubator for 3 hrs, after which the medium was removed by aspiration and pre-warmed 20% glycerol/ DMEM F12 medium (37° C.) added to each plate for 1 minute. After the glycerol exposure, the glycerol was removed from the plates and fresh medium added to each plate and then returned to the incubator. Cell culture fluid samples were collected 36, 60, 84, 108, and 132 hours post-transfection and immediately frozen at −20° C. for storage.

Experimental Design and Statistical Analysis.

The variables tested in the formation of calcium phosphate transfectacons were the concentrations of calcium, phosphate, and DNA as well as the pH of the co-precipitation reaction and the length of the reaction. The concentrations of calcium cation [Ca], phosphate anion [Pi], and DNA [DNA], and precipitation time were used to create a 3-level factorial design in which all combinations of these four variables were tested at low, medium, and high levels, thereby generating a $3^4$, or 81, total sets of conditions. The resulting data were analyzed using JMP statistical analysis software (SAS Institute, Inc., Cary, N.C.). Following the identification of phosphate concentration and length of co-precipitation as major variables affecting transiently-expressed protein titers, DNA and calcium concentrations were fixed at specific levels, while the preferred phosphate concentration and length of co-precipitation were determined using a central composite design. In this design, three variables were tested at five different levels that varied around a central value of 0.50 mM phosphate, 20 minutes co-precipitation time, and 3 hours exposure of cells to transfectacons. The data collected in this round of analysis were used to generate surface-response diagrams. Lastly, the effect of changes in the pH of co-precipitation reactions on transiently-expressed protein titers obtained using the selective conditions herein was investigated over the pH range of 6.75–7.35.

Protein Assays. The titers for the harvested cell culture fluid (HCCF) were assayed for the presence of either VEGF, DNase, E-25, or anti-HER-2 using respective ELISA assays described in Prince et al., *Clin. Exp. Immunol.*, 113: 289–296 (1998); Shifren et al., *J. Clin. Endo. Metab.*, 81: 3112–3118 (1996); Fox et al., *J. Pharm. Exp. Thera.*, 279: 1000–1008 (1996). Samples were diluted directly into assay diluent (PBS/0.5% BSA/0.05% P20/0.01% Thimerisol; PBS/0.5% BSA/0.05% P20; or PBS/0.5% BSA/0.01%P80/0.01% Thimerisol). For initial anti-HER-2 analysis, titers were normalized against control transfections that were performed for each set of transfections. These controls were transfections performed using the standard CaPi protocol with a precipitation time of 1 minute.

Results

Variables for Factorial Experimental Design.

In developing an experimental design for highly improved transient transfections using calcium phosphate as the transfecting reagent, the following variables were evaluated for their effect on the resulting titers of expressed protein product: length of co-precipitation reaction, and concentrations of calcium, phosphate, and DNA. These variables were examined at three levels (Table 1) that generate a total of 81 sets of combinations of conditions (Tables 2A–C) for initial screening of important variables. When a threshold level of expression of 200 μg/L was used to evaluate the resulting titers from the different combinations of variables, it was observed that with the exception of two sets of co-precipitation conditions (Run #s 31 and 34, Table 2B), all of the sets of conditions that met the threshold level for expression had lowered phosphate concentrations (0.5 mM) relative to the standard concentration of 0.75 mM phosphate (FIG. 1).

All co-precipitation reactions contained in Tables 2A–2C were conducted at 1.0 ml scale. Following specified precipitation times, reactions were diluted 5×with medium, then immediately added to 100-mm plates that contained an additional 5 ml of medium covering the adherent CHO cells. The transfections were grouped according to the phosphate concentrations in the co-precipitation reactions. Control transfections contained the following conditions: 125 mM calcium, 0.75 mM phosphate, 25 μg/mL plasmid DNA, and a precipitation time of 1 min. These controls were run in triplicate for each set of transfections and used to normalize the expression of anti-HER-2 over different days.

TABLE 1

Fractional Factorial Experimental Design Variables for Transient Transfections of CHO Cells Using CaPi/DNA as the Transfecting Reagent[a]

| Variables* | Low | Medium | High |
| --- | --- | --- | --- |
| Incubation Time | 1 min. | 5 min. | 20 min. |
| DNA Conc. (μg/ml) | 25 | 50 | 100 |
| [Ca++] (mM) | 125 | 188 | 250 |
| [Pi] (mM) | 0.5 | 0.75 | 1.0 |

[a]The total number of experimental combinations for a factorial involving four variables at three different levels is $3^4$ or 81 separate co-precipitation reactions.

TABLE 2A

Normalized Anti-HER-2 Expression for Transfections Performed Using 0.50 mM Phosphate in Co-precipitation Reactions[a]

| Run # | [Ca++] (mM) | [Pi] (mM) | [DNA] (μg/ml) | Time (min.) | Normalized Anti-HER-2 (μg/L) |
| --- | --- | --- | --- | --- | --- |
| (1) | 125 | 0.5 | 25 | 1 | 133.2 |
| (2) | 125 | 0.5 | 25 | 5 | 196.6 |
| (3) | 125 | 0.5 | 25 | 20 | 251.9 |
| (4) | 125 | 0.5 | 50 | 1 | 229.1 |
| (5) | 125 | 0.5 | 50 | 5 | 241.2 |

TABLE 2A-continued

Normalized Anti-HER-2 Expression for Transfections Performed Using 0.50 mM Phosphate in Co-precipitation Reactions[a]

| Run # | [Ca++] (mM) | [Pi] (mM) | [DNA] (μg/ml) | Time (min.) | Normalized Anti-HER-2 (μg/L) |
|---|---|---|---|---|---|
| (6)  | 125 | 0.5 | 50  | 20 | 198.1 |
| (7)  | 125 | 0.5 | 100 | 1  | 298.7 |
| (8)  | 125 | 0.5 | 100 | 5  | 152.8 |
| (9)  | 125 | 0.5 | 100 | 20 | 247.9 |
| (10) | 188 | 0.5 | 25  | 1  | 209.3 |
| (11) | 188 | 0.5 | 25  | 5  | 188.9 |
| (12) | 188 | 0.5 | 25  | 20 | 108.8 |
| (13) | 188 | 0.5 | 50  | 1  | 293.6 |
| (14) | 188 | 0.5 | 50  | 5  | 318.0 |
| (15) | 188 | 0.5 | 50  | 20 | 227.7 |
| (16) | 188 | 0.5 | 100 | 1  | 167.1 |
| (17) | 188 | 0.5 | 100 | 5  | 160.2 |
| (18) | 188 | 0.5 | 100 | 20 | 166.4 |
| (19) | 250 | 0.5 | 25  | 1  | 108.3 |
| (20) | 250 | 0.5 | 25  | 5  | 140.0 |
| (21) | 250 | 0.5 | 25  | 20 | 306.5 |
| (22) | 250 | 0.5 | 50  | 1  | 297.9 |
| (23) | 250 | 0.5 | 50  | 5  | 495.7 |
| (24) | 250 | 0.5 | 50  | 20 | 139.7 |
| (25) | 250 | 0.5 | 100 | 1  | 244.6 |
| (26) | 250 | 0.5 | 100 | 5  | 293.4 |
| (27) | 250 | 0.5 | 100 | 20 | 592.4 |

[a]The normalization factor for co-precipitation reactions and transfections containing 0.5 mM phosphate was calculated to be 1.0. The expression results for co-precipitation reactions 1–27, containing 0.5 mM Pi, can be cross-referenced (hashed bars) in FIG. 1, reactions 1–27, respectively.

TABLE 2B

Normalized Anti-HER-2 Expression for Transfections Performed Using 0.75 mM Phosphate in Co-precipitation Reactions[a]

| Run # | [Ca++] (mM) | [Pi] (mM) | [DNA] (μg/ml) | Time (min.) | Normalized Anti-HER-2 (μg/L) |
|---|---|---|---|---|---|
| (28) | 125 | 0.75 | 25  | 1  | 159.15 |
| (29) | 125 | 0.75 | 25  | 5  | 44.93  |
| (30) | 125 | 0.75 | 25  | 20 | 00.00  |
| (31) | 125 | 0.75 | 50  | 1  | 289.49 |
| (32) | 125 | 0.75 | 50  | 5  | 146.11 |
| (33) | 125 | 0.75 | 50  | 20 | 50.07  |
| (34) | 125 | 0.75 | 100 | 1  | 953.54 |
| (35) | 125 | 0.75 | 100 | 5  | 00.00  |
| (36) | 125 | 0.75 | 100 | 20 | 114.90 |
| (37) | 188 | 0.75 | 25  | 1  | 63.11  |
| (38) | 188 | 0.75 | 25  | 5  | 82.32  |
| (39) | 188 | 0.75 | 25  | 20 | 27.44  |
| (40) | 188 | 0.75 | 50  | 1  | 116.62 |
| (41) | 188 | 0.75 | 50  | 5  | 91.92  |
| (42) | 188 | 0.75 | 50  | 20 | 30.52  |
| (43) | 188 | 0.75 | 100 | 1  | 95.01  |
| (44) | 188 | 0.75 | 100 | 5  | 101.52 |
| (45) | 188 | 0.75 | 100 | 20 | 69.97  |
| (46) | 250 | 0.75 | 25  | 1  | 53.16  |
| (47) | 250 | 0.75 | 25  | 5  | 43.90  |
| (48) | 250 | 0.75 | 25  | 20 | 00.00  |
| (49) | 250 | 0.75 | 50  | 1  | 139.94 |
| (50) | 250 | 0.75 | 50  | 5  | 71.00  |
| (51) | 250 | 0.75 | 50  | 20 | 31.21  |
| (52) | 250 | 0.75 | 100 | 1  | 104.95 |
| (53) | 250 | 0.75 | 100 | 5  | 92.61  |
| (54) | 250 | 0.75 | 100 | 20 | 63.45  |

[a]The normalization factor for co-precipitation reactions and transfections containing 0.75 mM phosphate was calculated to be 3.4. The expression results for the above co-precipitation reactions 28–54 can be cross-referenced (black bars) in FIG. 1, reactions 1–27, respectively.

TABLE 2C

Normalized Anti-HER-2 Expression for Transfections Performed Using 1.0 mM Phosphate in Co-precipitation Reactions[a]

| Run # | [Ca++] (mM) | [Pi] (mM) | [DNA] (μg/ml) | Time (min.) | Normalized Anti-HER-2 (μg/L) |
|---|---|---|---|---|---|
| (55) | 125 | 1.0 | 25  | 1  | 77.49  |
| (56) | 125 | 1.0 | 25  | 5  | 45.41  |
| (57) | 125 | 1.0 | 25  | 20 | 31.9   |
| (58) | 125 | 1.0 | 50  | 1  | 134.1  |
| (59) | 125 | 1.0 | 50  | 5  | 59.26  |
| (60) | 125 | 1.0 | 50  | 20 | 39.90  |
| (61) | 125 | 1.0 | 100 | 1  | 82.50  |
| (62) | 125 | 1.0 | 100 | 5  | 94.18  |
| (63) | 125 | 1.0 | 100 | 20 | 45.89  |
| (64) | 188 | 1.0 | 25  | 1  | 65.70  |
| (65) | 188 | 1.0 | 25  | 5  | 51.00  |
| (66) | 188 | 1.0 | 25  | 20 | 40.08  |
| (67) | 188 | 1.0 | 50  | 1  | 98.12  |
| (68) | 188 | 1.0 | 50  | 5  | 74.51  |
| (69) | 188 | 1.0 | 50  | 20 | 43.43  |
| (70) | 188 | 1.0 | 100 | 1  | 82.31  |
| (71) | 188 | 1.0 | 100 | 5  | 55.16  |
| (72) | 188 | 1.0 | 100 | 20 | 41.68  |
| (73) | 250 | 1.0 | 25  | 1  | 85.33  |
| (74) | 250 | 1.0 | 25  | 5  | 63.48  |
| (75) | 250 | 1.0 | 25  | 20 | 55.69  |
| (76) | 250 | 1.0 | 50  | 1  | 39.33  |
| (77) | 250 | 1.0 | 50  | 5  | 29.31  |
| (78) | 250 | 1.0 | 50  | 20 | 28.51  |
| (79) | 250 | 1.0 | 100 | 1  | 49.67  |
| (80) | 250 | 1.0 | 100 | 5  | 83.57  |
| (81) | 250 | 1.0 | 100 | 20 | 30.64  |

[a]The normalization factor for co-precipitation reactions and transfections containing 1.0 mM phosphate was calculated to be 0.5. The expression results for the above co-precipitation conditions, 55–81, can be cross-referenced (dotted bars) in FIG. 1, reactions 1–27, respectively.

Statistical analysis of the complete factorial was performed and P-values were calculated for the influence of each variable on titers obtained in the experimental design. Small P-values, generally considered less than 0.05, suggest that the results of the factorial analysis are likely generated by the significance of the variables and not from random variation in the values obtained during data collection. The results (Table 3A) showed that of the variables tested in the co-precipitation reactions that affect transiently-expressed protein titers, phosphate concentration (P-value, <0.001) and length of co-precipitation reaction (P-value, <0.004) were the main variables, while the concentration of DNA in the reactions was not as significant a determinant (P-value, 0.047) in the outcome of the transfection. More importantly, the statistical analysis also revealed that there is an interaction between the phosphate concentration in a CaPi/DNA co-precipitation reaction and the length of the co-precipitation (P-value, 0.024), such that any change in the phosphate concentration requires a change in the length of the co-precipitation reaction to achieve the best level of expression. This novel finding of interaction clearly illustrates the power of using factorial analysis in experiments of the nature herein. A detailed analysis of the levels for the variables examined in this experiment is contained in Table 3C, and showed the influence of phosphate on the titers for anti-HER-2 as well as a time dependence for obtaining higher titers. The data used to calculate these mean titers included reactions at 1 ow, medium, and high levels for each of the time points studied. Note that as this data is further subdivided into phosphate and time groupings, the time-dependent relationship between the phosphate concentration in the co-precipitation reaction and titer for HER-2 expression is only observed for co-precipitation reactions with phosphate concentrations above 0.5 mM (Table 3D).

To rule out the possibility that the one large value obtained for one set of co-precipitation conditions (Table 2B, reaction 34) skewed the statistical analysis, the analysis was performed both with (Table 3A) and without (Table 3B) the data point and found not to change the results of the factorial analysis.

TABLE 3

Analysis of Factorial Experimental Design for Anti-HER-2 Transient Transfections[a]

TABLE 3A

ANOVA analysis of log transformed data excluding normalized Anti-HER-2 value of 953.54

| Source | DF | Partial SS | F Value | P-Value |
|---|---|---|---|---|
| CA | 2 | 0.39130663 | 0.28 | 0.7553 |
| **Pi | 2 | 36.62125549 | 26.42 | 0.0001 |
| **DNA | 2 | 4.29519617 | 3.10 | 0.0544 |
| **TIME | 2 | 7.42162944 | 5.35 | 0.0080 |
| CA*Pi | 4 | 1.95379599 | 0.70 | 0.5927 |
| CA*DNA | 4 | 2.00271464 | 0.72 | 0.5810 |
| CA*TIME | 4 | 1.99727483 | 0.72 | 0.5823 |
| Pi*DNA | 4 | 3.99468760 | 1.44 | 0.2354 |
| **Pi*TIME | 4 | 6.47755342 | 2.34 | 0.0690 |
| DNA*TIME | 4 | 4.73782161 | 1.71 | 0.1639 |

TABLE 3B

ANOVA analysis of log transformed data including normalized Anti-HER-2 value of 953.54

| Source | DF | Partial SS | F Value | P-Value |
|---|---|---|---|---|
| CA | 2 | 0.26645383 | 0.18 | 0.8367 |
| *Pi | 2 | 34.68900632 | 23.29 | 0.0001 |
| **DNA | 2 | 4.84507914 | 3.25 | 0.0473 |
| **TIME | 2 | 9.42692073 | 6.33 | 0.0036 |
| CA*Pi | 4 | 1.43529663 | 0.48 | 0.7489 |
| CA*DNA | 4 | 1.39771761 | 0.47 | 0.7580 |
| CA*TIME | 4 | 3.59275307 | 1.21 | 0.3204 |
| Pi*DNA | 4 | 4.46915969 | 1.50 | 0.2169 |
| **Pi*TIME | 4 | 9.25132564 | 3.11 | 0.0237 |
| DNA*TIME | 4 | 4.47420783 | 1.50 | 0.2164 |

[a]The log transformation of normalized anti-HER-2 titers for the factorial experimental design were analyzed using an ANOVA test of group variance. The variables that were tested for significance were calcium concentration (CA), phosphate concentration (Pi), DNA concentration (DNA), and length of co-precipitation (TIME). These variables were also tested in two-way interactions. Table 3A: ANOVA analysis of log transformed anti-HER-2 titers was performed excluding the value for reaction 34 (Table 2B). Pi and TIME appear to be the most influential factors in determining transiently-expressed protein titers, although the effect of one factor varies across the range of the other as indicated by the significant Pi*TIME interaction (double-asterisk-marked regions). DNA also appears influential, although possibly to a lesser extent. Table 3B: ANOVA analysis performed on log transformed anti-HER-2 titers including value for reaction 34 (Table 2B) confirms that this data point does not significantly influence the outcome of the experimental design. DF, degrees of freedom; Partial SS, partial sum of squares.

TABLE 3C

Main Effects for Log-Transformed Normalized HER-2 Expression

| Factor/Level | Mean | Original Scale** | Factor/Level | Mean | Original Scale** |
|---|---|---|---|---|---|
| Ca *(mM) | | | DNA (µg/mL) | | |
| 125 | 4.46 | 86.90 | 25 | 4.12 | >61.55 |
| 188 | 4.53 | 93.17 | 50 | 4.66 | 106.05 |
| 250 | 4.39 | 80.95 | 100 | 4.61 | 100.40 |
| (P-Value = 0.837)* | | | (P-Value.= 0.047)* | | |

TABLE 3-continued

Analysis of Factorial Experimental Design for Anti-HER-2 Transient Transfections[a]

| Pi (mM) | | | Time (min.) | | |
|---|---|---|---|---|---|
| 0.5 | 5.38 | 218.97 | 1 | 4.88 | 131.80 |
| 0.75 | 3.97 | 52.83 | 5 | 4.47 | 87.01 |
| 1 | 4.04 | 56.65 | 20 | 4.05 | 57.15 |
| (P-Value < 0.001)* | | | (P-Value < 0.004)* | | |

*Tests for effect on average log-transformed normalized transient anti-HER-2 expression by each factor.
**Means transformed back to original scale by exponentiation.

TABLE 3D

Pi*Time Interaction for Log-Transformed Normalized HER-2 Expression

| Factor/Level Combination | | | |
|---|---|---|---|
| Pi | Time | Mean | Original Scale** |
| 0.5 | 1 | 5.34 | 209.38 |
| 0.5 | 5 | 5.42 | 225.07 |
| 0.5 | 20 | 5.41 | 222.80 |
| 0.75 | 1 | 4.97 | 143.62 |
| 0.75 | 5 | 3.89 | 48.98 |
| 0.75 | 20 | 3.04 | 20.96 |
| 1 | 1 | 4.33 | 76.14 |
| 1 | 5 | 4.09 | 59.75 |
| 1 | 20 | 3.69 | 39.97 |
| (P-Value = 0.024)* | | | |

*Test for dependence of time on Pi concentration in affecting average log-normalized transient anti-HER-2 expression.
**Means transformed back to original scale by exponentiation.

Robustness of Transfections is Increased at Lower Phosphate Concentrations.

As noted above, there are many reports in the literature that standard or near-standard co-precipitation conditions yield highly-variable titers for transfections performed on different days with the same reagents (Sambrook et al., supra). The sets of co-precipitation combinations that yielded transient titers >200 µg/L were redone in an attempt to determine the degree of robustness of the transfection conditions. Robustness was measured as the transient titer of the second transfection expressed as a percent of initial titer achieved in the screening mode of the experimental design.

As shown in Table 4, the double-asterisked regions illustrate that a subset of the co-precipitation combinations yielded titers that were comparable between the two independent transfections. Of particular interest is the clustering (Table 4, Run #s 22, 23, 26) of high titers (approx. 300–550 µg/L), robustness (104–134W), increased calcium levels (250 mM), and decreased phosphate concentration (0.5 mM) in the co-precipitation reactions relative to the standard levels of 125 mM and 0.75 mM, respectively. It is important to note that although other sets of co-precipitation combinations (Table 4, Run #s 3, 7, 13, 14, 31, 58, 67) also are robust, those sets of combinations did not achieve the highest titers or are not practical for scaling.

TABLE 4

Anti-HER-2 Expression for Selected Combinations of Calcium-Phosphate/DNA Co-precipitation Conditions[a]

| Run# | [Ca++] (mM) | [Pi] (mM) | [DNA] (μg/mL) | Time (min.) | 1st Exp. Data (μg/L) | 2nd Exp. Data (μg/L) | % 1st Set Exp. |
|---|---|---|---|---|---|---|---|
| (28) | 125 | 0.75 | 25 | 1 | 46.4 | 112.7 | 242 |
| **(31) | 125 | 0.75 | 50 | 1 | 84.4 | 111.5 | 132 |
| (34) | 125 | 0.75 | 100 | 1 | 279.8 | 39.6 | 14 |
| **(3) | 125 | 0.50 | 25 | 20 | 252 | 211.3 | 83.7 |
| **(7) | 125 | 0.50 | 100 | 1 | 299 | 345.7 | 115 |
| (9) | 125 | 0.50 | 100 | 20 | 248 | 122.4 | 49 |
| **(13) | 188 | 0.50 | 50 | 1 | 294 | 264.3 | 89.7 |
| **(14) | 188 | 0.50 | 50 | 5 | 318 | 287.8 | 90.5 |
| (21) | 250 | 0.50 | 25 | 20 | 306 | 155.3 | 50.6 |
| **(22) | 250 | 0.50 | 50 | 1 | 298 | 401.5 | 134 |
| **(23) | 250 | 0.50 | 50 | 5 | 496 | 549.6 | 110 |
| **(26) | 250 | 0.50 | 100 | 5 | 293 | 307.4 | 104 |
| (27) | 250 | 0.50 | 100 | 20 | 592 | 365.9 | 61.8 |
| **(58) | 125 | 1.0 | 50 | 1 | 251 | 214.7 | 85 |
| **(67) | 188 | 1.0 | 50 | 1 | 184 | 197.6 | 107 |

[a]To test for robustness, observations were not normalized for day-to-day variations in anti-HER-2 expression. The numbers in parentheses under the Run# column refer to reaction numbers that are contained in Tables 2A–C. Double-asterisk-marked areas represent sets of conditions that resulted in at least 84–134% robustness between the two observations.

Lower Phosphate in Co-precipitation Reactions Coupled with Longer Precipitation Times Yields Hither Transient Protein Titers.

The observation that lower phosphate concentrations in co-precipitation reactions lead to higher titers for transiently-expressed proteins prompted further analysis of this variable. The interaction of phosphate concentration with length of precipitation time was analyzed by quantifying their effects on protein titers. These variables along with exposure time (the length of time that cells are exposed to transfectacons) were studied in a central composite design, where the variables were fixed at five different levels that varied around a median value for phosphate, length of co-precipitation, and length of exposure of cells to transfectacons (Table 5A).

As observed in the initial screening mode for main factors affecting transiently-expressed protein titers, it was observed that lowering the phosphate concentration from the standard 0.75 mM to 0.25 mM resulted in an increase in the expression of anti-HER-2 (Table 5B). Two reactions that only differ in the phosphate concentration of the co-precipitation reaction are shown in Table 5B (reactions 9 and 10). In this experiment, the difference in phosphate concentration (0.25 mM phosphate vs. 0.75 mM phosphate) resulted in a 10-fold difference in the observed titers for the transient expression of anti-HER-2. In addition to the very low (VL) value for phosphate concentration in reaction 9, low phosphate (L) of 0.40 mM in Table 5B, reaction 2, also resulted in higher titers relative to the standard phosphate concentration of 0.75 mM.

TABLE 5

Central Composite Design for Anti-HER-2 Expression with Calcium Phosphate as the Transfecting Reagent[a]

Table 5A
Variables for Central Composite Design

|  | VL | L | M | H | VH |
|---|---|---|---|---|---|
| [Pi] (mM) | 0.25 | 0.40 | 0.50 | 0.60 | 0.75 |
| Precip. (min.) | 5 | 10 | 20 | 30 | 40 |
| Exp. Time (hr.) | 0* | 1 | 3 | 5 | 6 |

Table 5B

| RUN # | [Ca++] (mM) | [DNA] (μg/mL) | [Pi] (mM) | Exposure Time (hrs.) | Precip. Time (min.) | Anti-HER-2 (μg/L) (4.5 days) |
|---|---|---|---|---|---|---|
| (1) | 250 | 50 | 0.40 | 1 | 10 | 370.1 |
| (2) | 250 | 50 | 0.40 | 1 | 30 | 549.8 |
| (3) | 250 | 50 | 0.40 | 5 | 10 | 290.0 |
| (4) | 250 | 50 | 0.40 | 5 | 30 | 230.8 |
| (5) | 250 | 50 | 0.60 | 1 | 10 | 531.0 |
| (6) | 250 | 50 | 0.60 | 1 | 30 | 455.2 |
| (7) | 250 | 50 | 0.60 | 5 | 10 | 205.6 |
| (8) | 250 | 50 | 0.60 | 5 | 30 | 205.3 |
| **(9) | 250 | 50 | 0.25 | 3 | 20 | 547.5 |
| **(10) | 250 | 50 | 0.75 | 3 | 20 | 53.5 |
| (11) | 250 | 50 | 0.50 | 0 | 20 | 27.1 |
| (12) | 250 | 50 | 0.50 | 6 | 20 | 395.8 |
| (13) | 250 | 50 | 0.50 | 3 | 5 | 334.6 |
| (14) | 250 | sO | 0.50 | 3 | 40 | 170.3 |
| (15) | 250 | 50 | 0.50 | 3 | 20 | 465.8 |
| (16) | 250 | 50 | 0.50 | 3 | 20 | 272.1 |
| (17) | 250 | 50 | 0.50 | 3 | 20 | 308.6 |
| (18) | 250 | 50 | 0.50 | 0 | 20 | 39.9 |
| (19) | 250 | 50 | 0.50 | 0 | 20 | 57.6 |
| (20) | 250 | 50 | 0.50 | 0 | 20 | 61.3 |

[a]Transient anti-HER-2 expression at fixed calcium concentration (250 mM) and DNA concentration (50 μg/mL) was analyzed in a central composite design that explored phosphate concentration (Pi), length of co-precipitation (Precip.), and length of exposure of cells to transfectacon (Exp. Time) at five levels: VL — very low; L — low; M — median; H — high; and VH — very high. Table 5A shows the levels for the variables used in this design. Table 5B shows HCCFcollected and submitted for anti-HER-2 ELISA 4.5 days post-transfection. The double-asterisk area highlights a reaction in which the [Pi] is 0.25 mM and the single-asterisk area highlights an identical reaction in which the [Pi] is at the standard level of 0.75 mM.

The set of conditions identified in this Example do not support shorter precipitation times as being most preferred for the highest transient expression of recombinant molecules. FIG. 2A shows the relationship between co-precipitation time and the phosphate concentration in the CaPi/DNA co-precipitation reaction as they relate to transient protein expression levels. At standard phosphate concentrations of 0.75 mM, shorter co-precipitation times are necessary to achieve maximum titers, but as the phosphate concentration is decreased in these reactions, the length of the co-precipitation must be increased to obtain higher titers (at 0.25 mM phosphate, an expression level is achieved that far exceeds that which is attainable at standard phosphate concentration). In addition to the relationship between phosphate concentration and co-precipitation time, the effect of varying exposure time and phosphate concentration on transient anti-HER-2 expression was also examined. FIG. 3 shows that for highly-improved transient expression, at 0.25 mM phosphate, the most preferred range for exposure time is between 3.0 and 4.5 hours. This range is very similar to that used in standard protocols.

Transient Transfections Performed with the Co-precipitation Conditions Herein are Less Sensitive to Varying PH.

Following the identification of a set of conditions that provided for enhanced transient expression of a test molecule, transfections performed with CaPi transfectacons formed over a pH range of 6.75–7.35 were examined to see whether they exhibited the exquisite sensitivity to very small changes in pH (>0.06 pH units) that was reported in Chen and Okayama, supra. FIG. 4 shows that the transient expressions of both anti-HER-2 and E-25 are resistant to the pH of the co-precipitation reaction over the range of 6.85–7.05. This is a marked improvement over reports in the literature that changes in pH of less than a pH unit result in up to a 6-fold reduction in transient expression (O'Mahoney and Adams, supra). The percent change in anti-HER-2 expression over this range is no more than 27%, while E-25 expression only varies by as much as 33% over the same range (FIG. 4).

The final test of the new set of conditions herein was to determine whether they resulted in an enhanced transient expression of other recombinant proteins relative to the older protocol. Table 6 demonstrates that the co-precipitation conditions herein resulted in increased levels of expression from 1.5 to 3.8-fold for all expression vectors tested versus transient transfections performed using standard or near-standard co-precipitation conditions. These results were highly reproducible for all vectors tested with the exception of DNase.

TABLE 6

Transient Expression of Various Proteins in Adherent CHO Cells Using Calcium Phosphate as the Transfecting Reagent[a]

| Product Plasmid | Mean µg/L in HCCF with Standard Co-precipitation Conditions | Mean µg/L in HCCF with Co-precipitation Conditions of this Invention | Fold Increase in Titers |
| --- | --- | --- | --- |
| VEGF | 10 | 15.35 | 1.53 |
| (Range) | (8.3–15) | (15–15.7) | |
| DNase | 118 | 255 | 2.16 |
| (Range) | (42–200) | (190–320) | |
| E-25 | 113 | 412 | 3.64 |
| (Range) | (94–124) | (410–414) | |
| Anti-HER-2 | 132 | 508 | 3.84 |
| (Range) | (18–265) | (470–547) | |

[a]Transient transfections were performed using two sets of co-precipitation conditions: (standard conditions) 125 mM calcium; 0.75 mM phosphate, 25 ug/mL plasmid DNA, and a 1-minute precipitation time; (new conditions) 250 mM calcium, 0.25 mM phosphate, 50 µg/mL DNA, and a 20-minute precipitation time. These conditions were used to prepare transfectacons for two transient transfections (separate days) of four test molecules: VEGF, DNase, E-25, and anti-HER-2. HCCF was collected 5.5 days post-transfection and submitted for ELISA.

Discussion

The use of conventional approaches to achieve highly-improved process parameters has yielded considerable information about numerous biochemical processes as well as provided insights into the inner workings of cells and cellular processes (Box et al., eds., *Statistics for Experimenters: An Introduction to Design, Data Analysis, and Model Building* (John Wiley and Sons: New York, N.Y., 1978)). Although the classical one-variable-at-a time strategy has been very useful, it has certain limitations: 1) it does not allow for the determination of interactions between variables; 2) it may not allow for the accurate identification of a most preferred set of conditions; and 3) it may lead to inaccurate extrapolations of data. In this Example, factorial experimental designs were employed to achieve selectively improved transient transfection of CHO cells using calcium phosphate as the transfecting reagent. Calcium phosphate has been used as a transfecting reagent for over 20 years, but it has not been widely considered for scaled production of recombinant proteins due to the difficulty in scaling the process as well as the wide variability in protein titers from day to day. The use of factorial experimental design to improve processes has allowed exploration of areas of the response surface for the transient expression of recombinant proteins and the variables studied, which had not been previously investigated.

It has been determined that the main factors in co-precipitation reactions that affect the transient expression of recombinant molecules are the concentration of phosphate in the reaction and the length of the co-precipitation, while DNA concentration affects the resulting titers to a lesser extent. The decision to exclude pH as a variable in the experimental design was made because previous work had shown CaPi transfections are exquisitely sensitive to small changes in the pH of the co-precipitation reaction (Yang and Yang, both references, supra; O'Mahoney and Adams, supra; Chen and Okayama, supra), and it was desired not to have pH mask the other effects being observed (Wilson et al., supra).

The relative insensitivity of the co-precipitation reaction using the newly-identified levels represents a major breakthrough because it allows for the setting of a pH specification of ±0.1 for the 2×Hepes-buffered saline used in these reactions. A pH specification of ±0.1 pH units for co-precipitation reactions conducted using standard conditions yields highly unpredictable results, whereas the new set of co-precipitation conditions herein results in titers that are more predictable. For calcium phosphate to be considered a viable option for large-scale transient transfections, the process preferably performs over a range of conditions and not at a narrowly defined set of parameters. These data lead to identification of a new set of conditions that are more amenable to scaling and that provide for the robust transient expression of protein with calcium phosphate as the transfecting reagent.

The set of conditions identified in the invention herein are scaleable, the results are robust, and the titers are increased by as much as 3.8-fold over conventional conditions for generating CaPi transfectacons for transient transfections. It is expected that the conditions can be applied to transfection of suspension-adapted mammalian cells. The new process is also less sensitive to variations in pH than reported for CaPi transfections of mammalian cells. Protocols that showed shorter time points for co-precipitation yielding higher transient titers (O'Mahoney and Adams, supra; Jordan et al., *Nucleic Acids Res.*, supra; Jordan et al., *Cytotechnology*, supra) would not be easily scaled when dealing with larger-volume co-precipitation reactions. For those protocols that included longer precipitation times, a lack of robustness and extreme variability in obtainable titers was often observed (Sambrook et al., supra). Other preferred protocols that appear in the literature also generated variable titers for transiently-expressed proteins (Wigler et al., *Cell*, supra; Strain and Wyllie, *Biochem. J.*, 218: 475, 482 (1984); Gaunitz et al., *Biotechnigues*, 20(5): 826–30, 32 (1996); Seelos, *Anal. Biochem.*, 245(1): 109–111 (1997)). The identification of co-precipitation conditions that are at least about 10 minutes in length, more preferably at least about 15 minutes in length, allows for a more controlled and reproducible process.

In the search for new and promising human pharmaceuticals, it becomes necessary to identify, clone, and express proteins rapidly, so that they may be placed in a variety of bioassays that elucidate function. Following the successful identification of an activity, it then becomes necessary to generate milligram to gram quantities of these molecules for testing in animal models. If speed is of the essence, a large-scale transient system for the generation of these molecules is highly desirable. Due to the findings of this invention, CaPi co-precipitation with nucleic acids is a more attractive transfection option for the transient expression of polypeptides due to the identification of a set of conditions that provides for a scaleable and robust production of recombinant polypeptides at a fraction of the expense incurred with other transfectacon-forming reagents (e.g., cationic lipids, commercial polymers, etc.).

What is claimed is:

1. A process for preparing transfectacons of calcium phosphate and a desired nucleic acid comprising:
    a. admixing calcium divalent cation, phosphate multivalent anion, and the desired nucleic acid to form a precipitation mixture, wherein the precipitation mixture comprises an initial phosphate anion concentration of about 0.2 to 0.5 mM; and
    b. incubating the precipitation mixture for about 10 to 60 minutes to form transfectacons comprising calcium phosphate and the desired nucleic acid.

2. The process of claim 1 wherein the precipitation mixture is formed in a host cell culture.

3. The process of claim 2 wherein after incubation the host cell culture is diluted, wherein the transfectacons grow at a rate lower than the rate at which they grew in the precipitation mixture, and after dilution, the host cell culture is incubated.

4. The process of claim 1 wherein the nucleic acid comprises a fragment encoding a polypeptide operable linked to a control sequence therefor.

5. The process of claim 4 wherein the control sequence is at least a promoter, the polypeptide is eukaryotic, and the recovered transfectacons are delivered to eukaryotic tissue or cells.

6. The process of claim 5 wherein the polypeptide is a mammalian polypeptide and the tissue or cells are mammalian.

7. The process of claim 6 wherein the polypeptide is a human polypeptide and the tissue or cells are human.

8. A transfectacon prepared by the process of claim 1.

9. A process for delivering desired nucleic acid to eukaryotic tissue or cells comprising introducing to the tissue or cells the transfectacon of claim 8.

10. A process for introducing a desired nucleic acid into a eukaryotic host cell comprising:
    a) admixing calcium divalent cation, phosphate multivalent anion, and the desired nucleic acid to form a precipitation mixture, wherein the precipitation mixture comprises an initial phosphate anion concentration of about 0.2 to 0.5 mM;
    b) incubating the precipitation mixture for about 10 to 60 minutes to form transfectacons comprising calcium phosphate and the desired nucleic acid;
    c) diluting the precipitation mixture and admixing it with a eukaryotic host cell lacking a cell wall to form a transfection mixture; and
    d) incubating the transfection mixture to allow the eukaryotic host cell to take up the transfectacons to form a transfected cell.

11. The process of claim 10 wherein the eukaryotic host cell is a mammalian cell.

12. The process of claim 10 wherein the cells are Chinese hamster ovary cells.

13. The process of claim 10 wherein the desired nucleic acid is DNA.

14. The process of claim 10 wherein the desired nucleic acid encodes a mammalian polypeptide.

15. The process of claim 14 wherein the polypeptide is a human polypeptide.

16. The process of claim 15 wherein the polypeptide is VEGF, DNase, t-PA, a glycosylation variant of t-PA, or an antibody to IgE or to HER-2.

17. The process of claim 10 wherein in step (b) the precipitation mixture is incubated for a period of about 15 to 30 minutes.

18. The process of claim 10 wherein in step (a) the precipitation mixture comprises an initial concentration of the desired nucleic acid of at least about 30–100 µg/ml.

19. The process of claim 10 wherein in step (a) the precipitation mixture comprises an initial calcium cation concentration of about 180 to 300 mM.

20. The process of claim 10 wherein in step (a) the precipitation mixture comprises an initial concentration of the desired nucleic acid of about 40 to 60 µg/ml and the calcium concentration is about 180 to 270 mM.

21. The process of claim 10 wherein in step (c) the diluting and admixing are done simultaneously.

22. The process of claim 10 wherein in step (c) the diluting is carried out before the admixing.

23. The process of claim 10 wherein the cells are adherent cells.

24. The process of claim 10 wherein the cells are suspension-adapted cells.

* * * * *

UNITED STATES PATENT AND TRADEMARK OFFICE
CERTIFICATE OF CORRECTION

PATENT NO.   : 6,140,128
DATED        : October 31, 2000
INVENTOR(S)  : Darien L. Cohen, David W. Kahn, Marjorie E. Winkler It is certified that error appears in the above-identified patent and that said Letters Patent is hereby corrected as shown below:

COLUMN 1:
Line 36, change "Smyth-Templeton" to --Templeton--

COLUMN 1:
Line 37, change "McCutchman" to --McCutchan--

COLUMN 1:
Line 40, change "Bachetti" to --Bacchetti--

COLUMN 28:
Line 57, change "475,482" to --475-482--

Signed and Sealed this

Twelfth Day of June, 2001

*Attest:*

NICHOLAS P. GODICI
*Attesting Officer*   Acting Director of the United States Patent and Trademark Office

UNITED STATES PATENT AND TRADEMARK OFFICE
CERTIFICATE OF CORRECTION

PATENT NO.    : 6,140,128
DATED         : October 31, 2000
INVENTOR(S)   : Darien L. Cohen, David W. Kahn, Marjorie E. Winkler It is certified that error appears in the above-identified patent and that said Letters Patent is hereby corrected as shown below:

Column 1:
Line 36, change "Smyth-Templeton" to --Templeton--
Line 37, change "McCutchman" to --McCutchan--
Line 40, change "Bachetti" to --Bacchetti--

Column 28:
Line 57, change "475,482" to --475-482--

Signed and Sealed this

Twenty-sixth Day of June, 2001

*Attest:*

NICHOLAS P. GODICI
*Attesting Officer*  *Acting Director of the United States Patent and Trademark Office*